United States Patent [19]

Bernareggi et al.

[11] Patent Number: 5,039,684

[45] Date of Patent: Aug. 13, 1991

[54] TETRAZOLE AMIDE DERIVATIVES OF HETEROCYCLIC ALKENYL ACID AND THEIR USE AS ANTIALLERGIC SUBSTANCES

[75] Inventors: Virgilio Bernareggi, Cologno Monzese; Fausto Bonifacio, Milan; Maurizio Fano, Bresso; Luciano Trabella, Pieve del Cairo; Giandomenico Battigelli, Bareggio; Davide Montagna, Milan, all of Italy

[73] Assignee: Valeas S. p. A., Milan, Italy

[21] Appl. No.: 483,728

[22] Filed: Feb. 23, 1990

[30] Foreign Application Priority Data

Feb. 24, 1989 [IT] Italy .................. 19562 A/89

[51] Int. Cl.$^5$ .................. C07D 403/14; A61K 31/41
[52] U.S. Cl. .................. 514/314; 514/340; 514/381; 546/176; 546/210; 548/251
[58] Field of Search ........ 548/251; 514/381, 314, 514/340; 546/176, 210

[56] References Cited

FOREIGN PATENT DOCUMENTS

| 0146243 | 6/1985 | European Pat. Off. |
| 0186367 | 7/1986 | European Pat. Off. |
| 0187487 | 7/1986 | European Pat. Off. |
| 0249236 | 12/1987 | European Pat. Off. |
| 638515 | 9/1983 | Switzerland |

Primary Examiner—David B. Springer
Attorney, Agent, or Firm—Birch, Stewart, Kolasch & Birch

[57] ABSTRACT

Tetrazole amide derivatives of heterocyclic alkenyl acids, of general formula

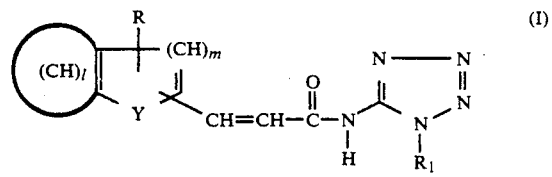

in which
Y=NH, O or S when m=1;
Y=N when m=2;
m=1 or 2;
l=0 or 4;
R=H, $C_{1-4}$ alkyl, Cl, Br, $CF_3$, $CH_2OCOCH_3$, or $OCH_2$-Ph;
$R_1$=H, alkaline metal or alkaline earth metal, the double bond of the alkenyl chain being of trans or cis configuration and the possible benzene ring being unsubstituted or substituted.

Such derivatives possess high antiallergic activity.

21 Claims, No Drawings

TETRAZOLE AMIDE DERIVATIVES OF HETEROCYCLIC ALKENYL ACID AND THEIR USE AS ANTIALLERGIC SUBSTANCES

FIELD OF THE INVENTION

This invention relates to compounds of tetrazole amide structure possessing antiallergic activity.

PRIOR ART

Disodium chromoglycate (DSCG) was the first compound representative of a new class of medicaments of antiallergic activity (J. S. G. Cox, 216, 1328, 1967).

DSCG is still used today as the chosen medicament in prophylaxis of allergic bronchial asthma or generally of type I allergic reactions to prevent release of the anaphylaxis chemical mediators.

This medicament has the drawback of not being absorbed at the gastro-enteric level and therefore in the clinical field it is used only in preparations for topical application.

The search for medicaments having activity and action mechanisms similar to DSCG but administrable orally and therefore of greater practical use has been the subject of numerous studies.

Various compounds of antiallergic activity are known in the literature, most of which have not found therapeutic application because of their poor power of action.

Those used in the clinical field include for example tranilast [N-(3', 4'-dimethoxycinnamoyl) anthranylic acid] which is able to provide dose-dependent inhibition of passive cutaneous anaphylaxis in the rat (PCA test) after oral administration of an $ED_{50}$ of 150 (88, 3–255) mg/kg/os when administered 2 hours before the challenge with the antigen (Koda et al., J. Allergy Clin. Immunol. 57, 396, 1976).

Products still under development which present good activity on oral administration in inhibiting passive cutaneous anaphylaxis in the rat include for example TA-5707 [6-methyl-N-(1H-tetrazol-5-yl)-2-pyridinecarboxyamide] of the Japanese company Tanabe Seiyaku. This compound has an $ED_{50}$ of 0.9 (0.6–1.6) mg/kg/os in inhibiting passive cutaneous anaphylaxis in the rat when administered orally 5 minutes before the challenge with the antigen (K. Tsuzurahara et al., Japan J. Pharmacol., 40, 37, 1986).

SUMMARY OF THE INVENTION

We have now discovered new tetrazole amide derivatives which provide high antiallergic activity. Said derivatives have the following general formula:

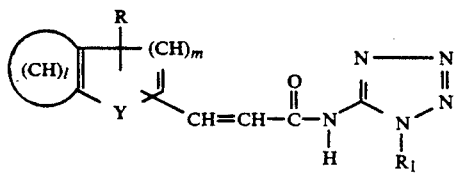

in which
- $Y=NH$, O or S when $m=1$;
- $Y=N$ when $m=2$;
- $m=1$ or 2;
- $l=0$ or 4;
- $R=H$, $C_{1-4}$ alkyl, Cl, Br, $CF_3$, $CH_2OCOCH_3$, or $OCH_2$-Ph;
- $R_1=H$, alkaline metal or alkaline earth metal, the double bond of the alkenyl chain being of trans or cis configuration and the possible benzene ring being unsubstituted or substituted.

The present invention also relates to the process for preparing the derivatives (I), their use as antiallergic substances and the therapeutic compounds which contain them as active substances.

DETAILED DESCRIPTION OF THE INVENTION

The characteristics and advantages of the present invention will be more apparent from the following detailed description of the process for preparing derivatives of formula (I) and their allergic activity tests.

The process for preparing the products of formula (I) is implemented in the following stages:

a) heterocyclic alkenyl acids of formula (II)

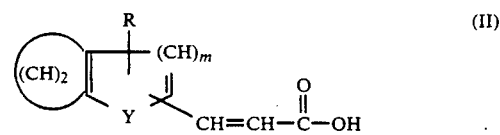

are prepared;

b) the acids of formula (II) are condensed directly with 5-aminotetrazole to give (I) where $R_1=H$, or are transformed into the respective chlorides of formula (XII)

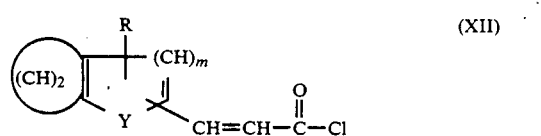

c) said chlorides (XII) are reacted with 5-aminotetrazole to give (I) where $R_1=H$;

d) the products (I) where $R_1=H$ are possibly salified.

In formulas (II) and (XII) and in the formulas given hereinafter R, Y and l have the meanings given heretofore for formula (I).

When $m=1$ and the double bond of the alkenyl chain is in TRANS configuration, the corresponding heterocyclic alkenyl acids are prepared using as starting substance the aldehydes of formula (III)

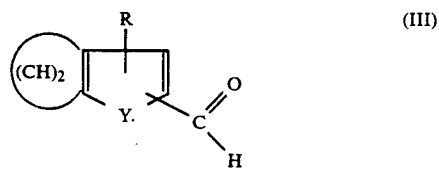

Said aldehydes are reacted with malonic acid in the presence of piperidine to give the alkenyl acids of formula (IV)

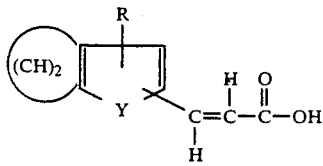
(IV)

The aforesaid reaction is conducted in anhydrous pyridine using a molar ratio of malonic acid to (III) of between 2 and 2.5 and preferably of between 2 and 2.1.

The reaction is conducted at a temperature of between 60° and 120° C. and preferably between 80° and 100° C. under energetic stirring for a period of time of between 2 and 8 hours.

A modification of the aforesaid reaction is to react the aldehydes of formula (III) with acetic anhydride and potassium or sodium acetate.

The molar ratio of anhydrous potassium or sodium acetate to (III) used is between 1 and 1.5 and preferably between 1 and 1.1, and of acetic anhydride to (III) is between 1.2 and 2 and preferably between 1.4 and 1.6.

The reaction is conducted at a temperature of between 90° and 190° C. and preferably between 100° and 150° C. under energetic stirring for a period of time of between 2 and 7 hours.

When $m=2$, $Y=N$ and $l=0$ or 4 and the double bond of the alkenyl chain is in trans configuration, the corresponding alkenyl acids can be prepared following an alternative synthesis path which as starting substances uses methyl derivatives of formula (V)

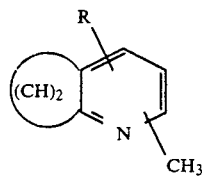
(V)

The methyl derivatives of formula (V) are reacted with $Cl_3CCHO$ to give the corresponding addition compounds of formula (VI)

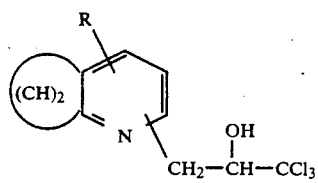
(VI)

The aforesaid reaction is conducted without the aid of particular solvents using a molar ratio of $Cl_3CCHO$ to (V) of between 0.8 and 1.5 and preferably between 0.95 and 1.3.

The reaction is conducted at a temperature of between 60° and 100° C. and preferably between 70° and 90° C. for a period of time of between 2 and 40 hours.

The compounds of formula (VI) are then subjected to hydrolysis to give the alkenyl acids of formula (VII)

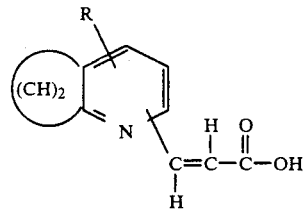
(VII)

The hydrolysis is conducted with an excess of alcoholic KOH (ethanol or methanol can be used as the alcohol), at a temperature of between 40° and 80° C. and preferably between 50° and 70° C., for a period of time of between 1 and 4 hours.

When $m=1$ and the double bond of the alkenyl chain is in cis configuration, the corresponding heterocyclic alkenyl acids are prepared using as starting substance the aldehydes of formula (III)

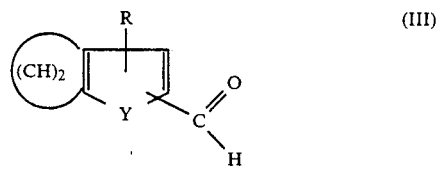
(III)

Said aldehydes are reacted with the ethyl monoester of malonic acid or alternatively with the methyl monoester of malonic acid in the presence of piperidine to give the ethyl or methyl esters respectively of alkenyl acids of formula (VIII) with the hydrogens of the double bond in trans position:

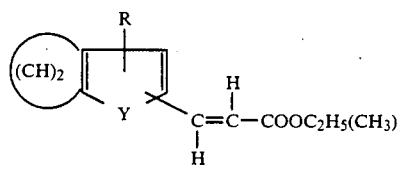
(VIII)

The aforesaid reaction is conducted in anhydrous pyridine using a molar ratio of malonic acid methyl monoester or alternatively malonic acid ethyl monoester to (III) of between 1 and 1.5 and preferably between 1 and 1.1.

The reaction is conducted at a temperature of between 60° and 120° C. and preferably between 60° and 80° C. under energetic agitation for a period of time of between 2 and 6 hours.

The ethyl or methyl esters of formula (VIII) are subjected to photochemical isomerization to give the corresponding esters of formula (IX) with the hydrogens of the double bond in the cis position

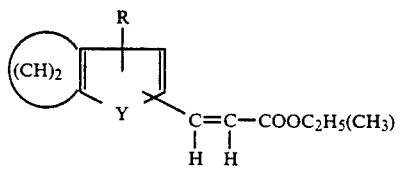
(IX)

The aforesaid reaction is conducted in a reaction medium consisting of an organic solvent such as acetonitrile, THF, acetone or DMF, acetonitrile being preferably used.

The irradiation source used is a high pressure mercury vapour lamp.

The irradiation time varies from half an hour to three hours.

The esters with cis configuration of formula (IX) are then saponified by conventional known methods to give the alkenyl acids of formula (IVA) with the hydrogens of the double bond in the cis position

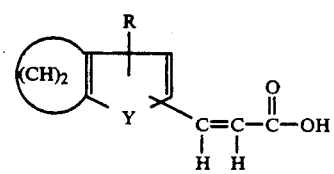
(IVA)

When m=2, Y=N and the double bond of the alkenyl chain is in the cis configuration the corresponding alkenyl acids are prepared using as starting substance the alkenyl acids of formula (VII) with the hydrogens of the double bond in the trans position

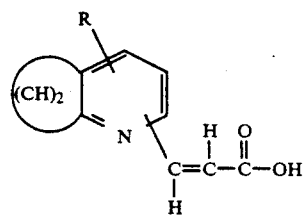
(VII)

These acids are transformed by known traditional methods into the methyl or ethyl esters of formula (X)

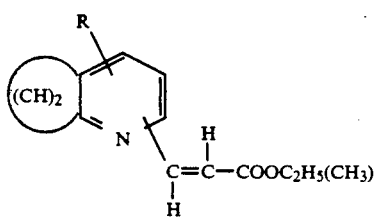
(X)

The methyl or ethyl esters of formula (X) are subjected to photochemical isomerization to give the corresponding esters of formula (XI) with the hydrogens of the double bond in the cis position

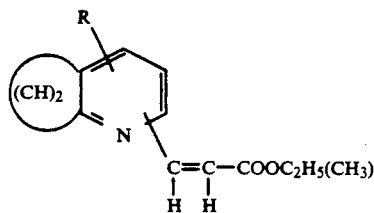
(XI)

The aforesaid reaction is conducted in a reaction medium consisting of an organic solvent such as acetonitrile, THF, acetone or DMF, acetonitrile being preferably used. The irradiation source used is a high pressure mercury vapour lamp.

The irradiation time varies from half an hour to 4 hours.

The esters with cis configuration of formula (XI) are then saponified by conventional known methods to give the alkenyl acids of formula (VIIA)

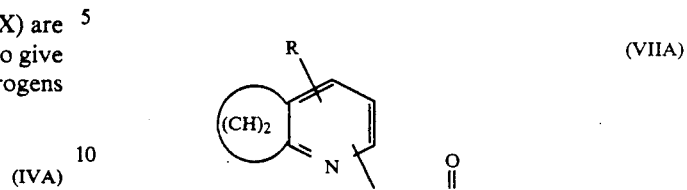
(VIIA)

As an alternative to the photochemical method for obtaining the cis-alkenyl acids of formula (IV A and VII A), one can employ as starting products acids of formula (XIII)

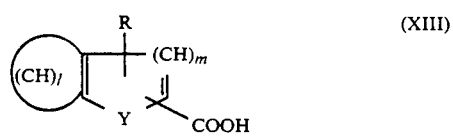
(XIII)

Said acids are first transformed into the corresponding chlorides of formula (XIV):

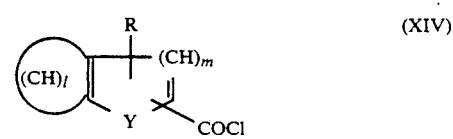
(XIV)

by treatment with conventional halides such a $SOCl_2$, $POCl_3$, $PCl_5$, or oxalyl chloride, under suitable conditions.

The chlorides of acids (XIV) are then reacted with methyl (triphenyl phosphoranilidene) acetate or alternatively with ethyl (triphenyl phosphoranilidene) acetate to yield the methyl, respectively ethyl ester of the phosphoranyl intermediates of formula (XV):

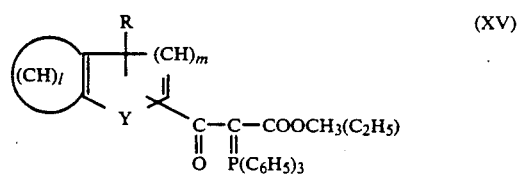
(XV)

The condesation is performed in freshly distilled benzene with a molar ratio between methyl (triphenyl phosphoranilidene) acetate, or alternatively ethyl (triphenyl phosphoranilidene) acetate and (XIV) between 1.5 and 2 and preferably between 1.8 and 2.

The reaction is carried out at temperatures between 10° and 30° C., and preferably between 20° and 25° C. under strong stirring, for a period of time between 3 and 5 hours.

The methyl or ethyl esters of formula XV are pyrolized under vacuum in a distillation apparatus to yield the corresponding propiolic esters of formula (XVI).

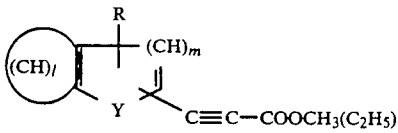

The pyrolysis and contemporaneous distillation of the esters of formula (XVI) is carried out at a temperature of between 200° and 250° C. and preferably between 210° and 230° C., and under a residual pressure of between 0 and 10, and preferably between 5 and 8 mmHg.

The triple bond of compound (XVI) may be conveniently reduced by treatment with hydrogen under pressure, in the presence of a suitable catalyst, as for instance 5% Pd/BaSO₄.

This reaction leads to esters having cis configuration of formula (IX) and (XI).

These esters, as previously described, are saponified to yield the alkenyl acids of formula (IV A) and (VII A).

Subsequently, according to the preferred process, the acids of formula (IV), (VII), (IVA) and (VIIA) corresponding to general formula (I) are firstly transformed into the corresponding chlorides of formula (XII):

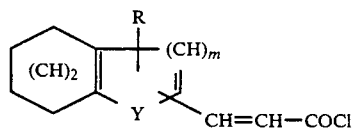

by treatment with conventional halogenants such as $CSOCl_2$, $POCl_3$, $PCl_5$ or oxalyl chloride under suitable conditions.

If the acids (IVA) and (VIIA) are used in formula (XII) the hydrogens of the double bond of the alkenyl chain are in cis configuration.

The next stage consists of condensing the chlorides of the acids (XII) with 5-aminotetrazole to give the products of general formula (I) where $R_1 = H$.

The reaction of this stage is conducted in a reaction medium consisting of an organic solvent.

Examples of solvents which can be used are chloroform, benzene, toluene, tetrahydrofuran, dioxane and dimethylformamide, the preferred solvents being toluene and teterahydrofuran.

For the reaction a molar ratio of 5-aminotetrazole to (XII) of between 2 and 2.5 is used, and preferably between 2 and 2.1.

The reaction is conducted at a temperature of between 40° and 150° C. and preferably 50° and 120° C., under stirring for a period of time of between 2 and 7 hours.

A modification of the aforesaid condensation reaction is to directly treat the acids of formula (IV) or (VII) or (IVA) or (VIIA) with the 5-aminotetrazole.

This reaction is conducted in a reaction medium consisting of an organic solvent in the presence of a condensing agent.

Solvents such as tetrahydrofuran, pyridine and dimethylformamide can be used as the reaction medium, pyridine preferably being used.

The condensing agents which can be used include dicyclohexylcarbodiimide, silicon tetrachloride and carbonyldiimidazole, the preference being for dicyclohexylcarbodiimide.

The molar ratio of the 5-aminotetrazole to the compounds (IV) or (VII) or (IVA) or (VIIA) is between 1 and 1.5 and preferably between 1 and 1.1.

The reaction is conducted at a temperature of between 40° and 100° C. and preferably between 60° and 100° C. for a period of time of between 2 and 10 hours.

The products of general formula (I) where $R_1 = H$ can if desired be salified to alkaline or alkaline earth metal salts following the usual procedures to give the products of general formula (I) where $R_1$ = alkaline or alkaline earth metal.

On the basis of the description, all possible variations, which are all included within the scope of the invention, are immediately apparent to the expert of the art.

Some examples of the method of preparation of the new compounds are given hereinafter to illustrate some preferred embodiments of the present invention.

The invention is illustrated but not limited by said examples.

The pharmacological trials reported hereinafter show that the compounds of the invention have high antiallergic activity and very low toxicity. They can therefore be used as active substances in the preparation of pharmaceutical compounds of antiallergic activity, in association with diluents and excipients normally used in the pharmaceutical field.

EXPERIMENTAL PART

EXAMPLE 1

3-(5-METHYL-2-THIENYL)ACRYLIC ACID TRANS ISOMER 34 g of 5-methyl-2-thiophenecarboxyaldehyde (0.27 moles) dissolved in 136 ml of anhydrous pyridine, 56.2 g of malonic acid (0.54 moles) and 2.72 ml of piperidine are placed in a previously dried flask fitted with a mechanical stirrer.

The reaction mixture is heated to 80°-90° C. for 7 hours. After this the hot solution is dripped under strong stirring into 2 liters of water-ice previously acidified to pH 1 with concentrated HCl.

The precipitated solid is filtered off through a Buchner funnel, washed with water and dried in an oven.

38 g of 3-(5-methyl-2-thienyl)acrylic acid trans isomer are obtained (yield 83.7%, M.P. 167°-168° C., H⁺ titre 99%).

| Analysis for $C_8H_8O_2S$ | | |
|---|---|---|
| | % calculated | % found |
| C | 57.12 | 56.94 |
| H | 4.79 | 4.84 |
| S | 19.06 | 19.20 |

The following compounds in trans isomer form are prepared in a manner analogous to the aforesaid example:
3-(2-thenyl)acrylic acid
3-(5-ethyl-2-thienyl)acrylic acid
3-(5-bromo-2-thienyl)acrylic acid
3-(4-chloro-2-thienyl)acrylic acid
3-(4-butyl-2-thienyl)acrylic acid
3-(3-chloro-2-thienyl)acrylic acid
3-(3-bromo-2-thienyl)acrylic acid.

EXAMPLE 2

3-(3-THIENYL)-ACRYLIC ACID TRANS ISOMER 50 g of 3-thiophene carboxyaldehyde (0.45 moles), 68.85 g of acetic anhydride (0.675 moles) and 44.16 g of powdered potassium acetate (0.45 moles) are mixed in the reaction flask.

The reaction mixture is kept stirred and is heated with an oil bath to 150° C. for 3 hours without interruption.

After slight cooling, the mixture is treated with 2.4 liters of water, the solution obtained being acidified to pH 1 with concentrated hydrochloric acid and the precipitate formed being filtered off through a Buchner funnel and dried.

53.7 g of 3-(3-thienyl)-acrylic acid trans isomer are obtained (yield 77.5%, M.P. 157°–159° C., H+ titre 99.6%).

| Analysis for $C_7H_6O_2S$ | | |
|---|---|---|
| | % calculated | % found |
| C | 54.52 | 54.80 |
| H | 3.92 | 3.98 |
| S | 20.79 | 20.81 |

The following compounds in trans isomer form are prepared in a manner analogous to the aforesaid example:
3-(5-ethyl-3-thienyl)-acrylic acid
3-(5-methyl-3-thienyl)-acrylic acid
3-(5-bromo-3-thienyl)-acrylic acid
3-(4-chloro-3-thienyl)-acrylic acid
3-(4-propyl-3-thienyl)-acrylic acid
3-(4-methyl-3-thienyl)-acrylic acid
3-(2-bromo-3-thienyl)-acrylic acid.

EXAMPLE 3

3-(2-PYRROLE)-ACRYLIC ACID TRANS ISOMER 10 g of 2-pyrrole carboxaldehyde (0.105 moles), 21.84 g of malonic acid (0.21 moles), 50 ml of anhydrous pyridine and 0.8 ml of piperidine are mixed in a previously dried flask provided with a mechanical stirrer.

The reaction mixture is heated to 90° C. for 5 hours, after which it is dripped hot into 750 ml of water-ice previously acidified to pH 1 with concentrated hydrochloric acid.

The precipitated solid obtained is filtered off through a Buchner funnel, washed with water and dried.

The solid obtained is crystallized with 200 ml of ethanol.

7.3 g of 3-(2-pyrrole)-acrylic acid trans isomer are obtained (yield 50.74%, M.P. 170°–172° C.).

| Analysis for $C_7H_7NO_2$ | | |
|---|---|---|
| | % calculated | % found |
| C | 61.30 | 61.08 |
| H | 5.14 | 5.27 |
| N | 10.21 | 10.09 |

EXAMPLE 4

3-(2-PYRIDYL)-ACRYLIC ACID TRANS ISOMER 30.81 g of 2-pyridine carboxaldehyde (0.288 moles), 29.95 g of malonic acid (0.288 moles), 1 ml of piperidine and 30 ml of anhydrous pyridine are mixed in a dry apparatus.

The mixture is left at ambient temperature for 1 hour after which 1000 ml of distilled water are added followed by ammonia to basic pH. The mixture is acidified with 1:1 hydrochloric acid to pH 4 and the precipitated solid filtered off through a Buchner funnel and dried.

20.34 g of 3-(2-pyridyl)-acrylic acid trans isomer are obtained (yield 47.4%, M.P. 204° C.).

| Analysis for $C_8H_7NO_2$ | | |
|---|---|---|
| | % calculated | % found |
| C | 64.42 | 64.28 |
| H | 4.73 | 4.93 |
| N | 9.39 | 9.12 |

The following compounds in trans isomer form are prepared in a manner analogous to the aforesaid example:
3-(6-methyl-2-pyridyl)-acrylic acid
3-(6-chloro-2-pyridyl)-acrylic acid
3-(6-benzyloxy-2-pyridyl)-acrylic acid
3-(5-methyl-2-pyridyl)-acrylic acid
3-(4-isopropyl-2-pyridyl)-acrylic acid
3-(4-ethyl-2-pyridyl)-acrylic acid
3-(4-benzyloxy-2-pyridyl)-acrylic acid
3-(4-bromo-2-pyridyl)-acrylic acid
3-(3-methyl-2-pyridyl)-acrylic acid
3-(3-chloro-2-pyridyl)-acrylic acid.

EXAMPLE 5

3-(3-PYRIDYL)-ACRYLIC ACID TRANS ISOMER 15 g of 3-pyridine carboxaldehyde (0.14 moles), 14.56 g of malonic acid (0.14 moles), 0.5 ml of piperidine and 15 ml of anhydrous pyridine are mixed in a dry apparatus.

The mixture is heated to 80° C. for 3 hours with an oil bath. After this time a fairly compact solid mass is formed and is taken up in water.

The undissolved solid is filtered off with a Buchner funnel, dried and chromatographed in a silica gel column using 9.5:0.5 chloroform:methanol as eluent. The fractions containing the pure product are pooled and evaporated to dryness. The solid residue is vacuum dried.

15.61 g of 3-(3-pyridyl)-acrylic acid trans isomer are obtained (yield 74.8%, M.P. 232°–234° C.).

| Analysis for $C_8H_7NO_2$ | | |
|---|---|---|
| | % calculated | % found |
| C | 64.42 | 64.38 |
| H | 4.73 | 4.77 |
| N | 9.39 | 9.41 |

The following compounds in trans isomer form are prepared in a manner analogous to the aforesaid example:
3-(6-methyl-3-pyridyl)-acrylic acid
3-(6-chloro-3-pyridyl)-acrylic acid
3-(6-benzyloxy-3-pyridyl)-acrylic acid
3-(5-methyl-3-pyridyl)-acrylic acid
3-(4-isopropyl-3-pyridyl)-acrylic acid
3-(4-ethyl-3-pyridyl)-acrylic acid
3-(4-bromo-3-pyridyl)-acrylic acid
3-(2-methyl-3-pyridyl)-acrylic acid
3-(2-chloro-3-pyridyl)-acrylic acid.

EXAMPLE 6

1-(4-PYRIDYL)-2-HYDROXY-3,3,3-TRICHLOROPROPANE 60 g of γ-picoline (0.645 moles) are placed in a flask and mixed with 3 g of Norit decolorizing carbon after which 88.98 g of chloral (0.60 moles) are added dropwise and the obtained suspension is vigorously stirred.

When the addition is complete the mixture is heated to 40° C. for 32 hours and to 70° C. for 8 hours.

The reaction mixture is treated with 250 ml of water previously acidified with 75 ml of concentrated HCl. The mixture is allowed to digest for 2 hours after which it is heated to boiling for 5 minutes and filtered.

The filtrate is neutralized with a sodium carbonate solution to precipitate a solid which is filtered through a Buchner funnel, washed with water and dried.

The solid is crystallized with 200 ml of ethyl acetate.

95 g of 1-(4-pyridyl)-2-hydroxy-3,3,3-trichloropropane are obtained (yield 65.8%, M.P. 166°–168° C.).

| | Analysis for $C_8H_8Cl_3NO$ | |
|---|---|---|
| | % calculated | % found |
| C | 39.94 | 39.78 |
| H | 3.35 | 3.52 |
| N | 5.82 | 5.60 |

3-(4-PYRIDYL)-ACRYLIC ACID TRANS ISOMER 95 g of 1-(4-pyridyl)-2-hydroxy-3,3,3-trichloropropane (0.40 moles) are placed in an anhydrous apparatus and dissolved under hot conditions with 700 ml of anhydrous ethanol.

The solution is cooled to 20° C. after which 135 g of KOH (2.41 moles) dissolved in 700 ml of anhydrous ethanol are added, the solution is stirred and heated to between 40° and 50° C. for 2 hours and to 60° C. for a further 2 hours.

The precipitate which forms is removed by filtration and the filtrate is evaporated to dryness.

The solid residue is taken up with 400 ml of water. The solution obtained is heated to boiling and acidified with acetic acid until precipitation begins.

The solid obtained is filtered and compressed to remove most of the water and then dissolved in the minimum quantity of hot diluted ammonium hydroxide.

Acetic acid is added to the solution obtained and the precipitate which forms is filtered off and dried.

44.1 g of 3-(4-pyridyl)-acrylic acid trans isomer are obtained (yield 74%, M.P. 300° C. dec.).

| | Analysis for $C_8H_7NO_2$ | |
|---|---|---|
| | % calculated | % found |
| C | 64.42 | 64.29 |
| H | 4.73 | 4.93 |
| N | 9.39 | 9.20 |

The following compounds in trans isomer form are prepared in a manner analogous to the aforesaid example:
3-(2-methyl-4-pyridyl)-acrylic acid
3-(2-ethyl-4-pyridyl)-acrylic acid
3-(3-methyl-4-pyridyl)-acrylic acid
3-(2-benzyloxy-4-pyridyl)-acrylic acid
3-(3-acetoxymethyl-4-pyridyl)-acrylic acid
3-(2-chloro-4-pyridyl)-acrylic acid
3-(3-chloro-4-pyridyl)-acrylic acid.

EXAMPLE 7

3-(2-FURYL) ACRYLIC ACID TRANS ISOMER 288 g of furfural (3 moles) are mixed in a suitable reaction flask with 460 g of acetic anhydride (4.51 moles) and 294 g of powdered potassium acetate (3 moles).

The mixture obtained is kept stirred and is heated with an oil bath to 150° C. for 4 hours.

After slight cooling, the reaction mixture is treated with 3.5 liters of water, the solution obtained is acidified to pH 1 with concentrated HCl and the precipitate formed is filtered off through a Buchner funnel, washed with water and dried.

280 g of 3-(2-furyl) acrylic acid trans isomer are obtained (yield 67.6%, M.P. 138°–139° C., H+ titre 99.7%).

| | Analysis for $C_7H_6O_3$ | |
|---|---|---|
| | % calculated | % found |
| C | 60.87 | 60.99 |
| H | 4.38 | 4.30 |

EXAMPLE 8

3-(5-METHYL-FURYL) ACRYLIC ACID TRANS ISOMER 11 g of 5-methyl furfural (0.1 moles), 20.8 g of malonic acid (0.2 moles), 0.5 ml of piperidine and 80 ml of anhydrous pyridine are introduced into an anhydrous apparatus kept under a stream of nitrogen.

The suspension obtained is heated to 90° C. for 4 hours under strong stirring.

After this the reaction mixture is dripped hot into one liter of water-ice previously acidified to pH 1 with concentrated hydrochloric acid. The solid which separates is filtered off through a Buchner funnel, dried and crystallized from acetone.

12.9 g of 3-(5-methyl-2-furyl) acrylic acid trans isomer are obtained (yield 84.8%, M.P. 163°–164° C., H+ titre 98.4%)

| | Analysis for $C_{10}H_{12}O_3$ | |
|---|---|---|
| | % calculated | % found |
| C | 66.65 | 66.77 |
| H | 6.71 | 6.91 |

The following compounds in trans isomer form are prepared in a manner analogous to the two aforesaid example:
3-(5-acetoxymethyl-2-furyl) acrylic acid
3-(5-benzyloxy-2-furyl) acrylic acid.

EXAMPLE 9

3-(3-INDOLYL) ACRYLIC ACID TRANS ISOMER 6.5 g of 3-(3-indole) carboxaldehyde (0.045 moles), 9.36 g of malonic acid (0.09 moles), 0.5 ml of piperidine and 40 ml of anhydrous pyridine are introduced into an anhydrous apparatus kept under a stream of nitrogen. The suspension obtained is heated to 90° C. for 3 hours under strong stirring.

After this, the reaction mixture is dripped hot into 800 ml of water-ice previously acidified to pH 1 with concentrated HCl.

The precipitated solid is filtered off with a Buchner funnel, dried and chromatographed in a silica gel column using 9.5:0.5 chloroform:methanol as eluent. The fractions containing the pure product are pooled and evaporated to dryness. 6.58 g of 3-(3-indolyl) acrylic acid trans isomer are obtained (yield 78.2%, M.P. 184°–186° C.).

| | Analysis for $C_{11}H_9NO_2$ | |
|---|---|---|
| | % calculated | % found |
| C | 70.57 | 70.41 |
| H | 4.85 | 4.79 |
| N | 7.48 | 7.36 |

EXAMPLE 10

1-(2-QUINOLYL)-2-HYDROXY-3,3,3-TRICHLORO PROPANE 45 g of quinaldine (0.31 moles) and 30 ml of anhydrous pyridine are introduced into an anhydrous apparatus kept under a stream of nitrogen. 60 g of chloral (0.406) are dripped into this solution, which is then heated with a oil bath to 80° C. for 2 hours.

On termination of the reaction the mixture is poured into a large quantity of iced water, the precipitate which forms being filtered off through a Buchner funnel and washed with water.

After drying, the solid is crystallized with 500 ml of ligroin.

71.3 g of 1-(2-quinolyl)-2-hydroxy-3,3,3-trichloro propane are obtained (yield 79%, M.P. 156°–158° C.).

| | Analysis for $C_{12}H_{10}Cl_3NO$ | |
|---|---|---|
| | % calculated | % found |
| C | 49.59 | 49.36 |
| H | 3.47 | 3.61 |
| N | 4.82 | 4.68 |

3-(2-QUINOLYL) ACRYLIC ACID TRANS ISOMER

A solution of 71.3 g of 1-(2-quinolyl)-2-hydroxy-3,3,3-trichloro propane (0.245 moles) in 600 ml of ethanol is dripped into a solution of 90 g of KOH (1.6 moles) in 360 ml of ethanol.

When the addition is complete the mixture is heated to 60° C. for 1 hour and the precipitated KCl filtered off while hot.

After one day at ambient temperature the potassium salt of 3-(2-quinolyl) acrylic acid precipitates in the reaction mixture and is filtered off through a Buchner funnel, taken up in 100 ml of ethanol and acidified with HCl gas in ethanol until precipitation begins.

The precipitate is crystallized with 256 ml of ethanol.

33 g of 3-(2-quinolyl) acrylic acid trans isomer are obtained (yield 67.7%, M.P. 195°–197° C.).

| | Analysis for $C_{12}H_9NO_2$ | |
|---|---|---|
| | % calculated | % found |
| C | 72.35 | 72.26 |
| H | 4.55 | 4.50 |
| N | 7.03 | 7.29 |

EXAMPLE 11

1-(4-QUINOLYL)-2-HYDROXY-3,3,3-TRICHLORO PROPANE 40 g of lepidine (0.28 moles) are dissolved in 100 ml of anhydrous pyridine in an anhydrous apparatus kept under a stream of nitrogen. 44 g of cloral (0,30 moles) are dripped into this solution, which is then heated to 85°–90° C. for 2 hours.

On termination of heating, the reaction mixture is poured into 500 ml of water-ice under strong stirring.

The precipitate which forms is filtered off through a Buchner funnel, washed with water and dried.

The solid obtained is crystallized twice with 292 ml of ethanol.

52.3 g of 1-(4-quinolyl)-2-hydroxy-3,3,3-trichloro propane are obtained (yield 64%, M.P. 190°–192° C.).

| | Analysis for $C_{12}H_{10}Cl_3NO$ | |
|---|---|---|
| | % calculated | % found |
| C | 49.59 | 49.86 |
| H | 3.47 | 3.70 |
| N | 4.82 | 4.97 |

3-(4-QUINOLYL) ACRYLIC ACID TRANS ISOMER

A solution of 65 g of KOH (1.16 moles) in 300 ml of ethanol is cautiously dripped into a solution of 65 g of 1-(4-quinolyl)-2-hydroxy-3,3,3-trichloro propane (0.22 moles) in 500 ml of ethanol.

When the addition is complete, the mixture is heated to 60° C. for 2 hours and the KCl which forms is filtered off through a Buchner funnel and washed with absolute ethanol.

The filtrate is diluted with an equal volume of water and the alcohol is removed by evaporation under reduced pressure.

The residual aqueous solution is decolorized with carbon and 50% acetic acid is added. The solid which separates is filtered off and treated under hot conditions with an aqueous sodium carbonate solution.

50% acetic acid is again added to the solution obtained and the precipitate which forms is filtered off and recrystallized with 100 ml of glacial acetic acid.

25.4 g of 3-(4-quinolyl) acrylic acid trans isomer are obtained (yield 58%, M.P. 276°–277° C.).

| | Analysis for $C_{12}H_9NO_2$ | |
|---|---|---|
| | % calculated | % found |
| C | 72.35 | 72.28 |
| H | 4.55 | 4.61 |
| N | 7.03 | 6.99 |

EXAMPLE 12

3-(5-METHYL-2-THIENYL) ACRYLOYL CHLORIDE TRANS ISOMER 10 g of 3-(5-methyl-2-thienyl) acrylic acid trans isomer (0.059 moles) prepared in accordance with Example 1) are mixed with 40.77 g of freshly distilled thionyl chloride (0.345 moles) in a dry apparatus under a stream of nitrogen.

The mixture is heated under reflux for 7 hours under strong stirring.

The reaction mixture is cooled and the excess thionyl chloride is distilled under reduced pressure.

The residue is washed several times with N-hexane and then completely dried to obtain a semi solid which solidifies completely at low temperature.

6.32 g of 3-(5-methyl-2-thienyl) acryloyl chloride trans isomer are obtained (yield 57.4%, $Cl^-$ titre 99.6%).

| | Analysis for $C_8H_7ClOS$ | |
|---|---|---|
| | % calculated | % found |
| C | 51.47 | 51.21 |
| H | 3.78 | 3.94 |
| S | 17.17 | 17.23 |

N-1H-TETRAZOL-5-YL-[3-[5-METHYL-(2-THIENYL)]] ACRYLAMIDE TRANS ISOMER (VAL 47-005)

5 g of 5-amino tetrazole monohydrate (0.048 moles) are mixed with 145 ml of tetrahydrofuran and 7.3 ml of water. The suspension is heated to 45° C. and when this becomes clear a solution of 4.47 g of 3-(5-methyl-2-thienyl) acryloylchloride trans isomer (0.024 moles) in 50 ml of tetrahydrofuran is dripped in.

When the addition is complete the mixture is heated under reflux for 2 hours after which 100 ml of water are added and the reaction flask placed in a refrigerator overnight.

The precipitate obtained is filtered off through a Buchner funnel and treated at about 80° C. with a 5% aqueous sodium bicarbonate solution (400 ml).

The resultant solution is cooled and acidified to pH 1 with concentrated HCl. The separated solid is filtered off and dried. 5.47 g of N-1H-tetrazol-5-yl-[3-[5-methyl-(2-thienyl)]] acrylamide trans isomer are obtained (yield 48%, M.P. 286°-288° C., U.V. titre 99.6%).

| | Analysis for $C_9H_9N_5OS$ | |
|---|---|---|
| | % calculated | % found |
| C | 45.94 | 45.78 |
| H | 3.85 | 3.77 |
| N | 29.77 | 29.76 |
| S | 13.63 | 13.81 |

N-1H-TETRAZOL-5-YL-[3-[5-METHYL-(2-THIENYL)]] ACRYLAMIDE SODIUM SALT TRANS ISOMER (VAL 47-005 SODIUM SALT)

2 g of N-1H-tetrazol-5-yl-[3-[5-methyl-(2-thienyl)]] acrylamide trans isomer (0.0085 moles) are suspended in an aqueous 2% sodium bicarbonate solution (18 ml) and heated under reflux until completely dissolved.

After cooling the solution a precipitate forms which is filtered off through a Buchner funnel and dried.

1.9 g of N-1H-tetrazol-5-yl-[3-[5-methyl-(2-thienyl)]] acrylamide sodium salt trans isomer are obtained (yield 87%, M.P. >300° C. dec.).

| | Analysis for $C_9H_8N_5NaOS$ | |
|---|---|---|
| | % calculated | % found |
| C | 42.01 | 41.77 |
| H | 3.13 | 3.18 |
| N | 27.22 | 27.20 |
| S | 12.46 | 12.41 |

EXAMPLE 13

N-1H-TETRAZOL-5-YL-[3-(2-THIENYL)] ACRYLAMIDE TRANS ISOMER (VAL 47-024)

10 g of 3-(2-thienyl) acrylic acid trans isomer (0.065 moles) (prepared as in Example 1) dissolved in 15 ml of anhydrous pyridine, and 6.69 g of 5-amino tetrazole monohydrate (0.065 moles) dissolved in 76 ml of anhydrous pyridine are placed in a dry apparatus kept under a stream of nitrogen.

The mixture temperature is raised to 60° C. and 13.42 g of dicyclohexylcarbodiimide (0.065 moles) dissolved in 15 ml of anhydrous pyridine are dripped in. The reaction temperature is maintained at 60° C. for 4 hours.

After this period the precipitate which forms is removed by filtration, the filtrate is evaporated to dryness under reduced pressure and the residue ground with 200 ml of ethyl acetate, filtered and dried.

9.47 g of N-1H-tetrazol-5-yl-[3-(2-thienyl)] acrylamide trans isomer are obtained (yield 65.9%, M.P. 287° C., U.V. titre 99.4%).

| | Analysis for $C_8H_7N_5OS$ | |
|---|---|---|
| | % calculated | % found |
| C | 43.42 | 43.52 |
| H | 3.19 | 3.09 |
| N | 31.65 | 31.52 |
| S | 14.49 | 14.12 |

EXAMPLE 14

N-1H-TETRAZOL-5-YL-[3-[5-BROMO-(2-THIENYL)]]-ACRYLAMIDE TRANS ISOMER (VAL 47-008)

A mixture composed of 5 g of 3-(5-bromo-2-thienyl) acrylic acid trans isomer (prepared as in Example 1) (0.021 moles), 6.8 g of 1,1'-carbonyldiimidazole (0,042 moles) and 100 ml of anhydrous dimethylformamide is heated to 90°-100° C. under a nitrogen atmosphere for 1.5 hours.

After heating, 2.163 g of 5-amino tetrazole monohydrate (0.021 moles) dissolved in 40 ml of anhydrous dimethylformamide are dripped in, and the resultant mixture is heated to 100° C. for 3 hours.

The solvent is evaporated and the solid residue chromatographed in a silica gel column using 6:3:0.5 chloroform/methanol/ammonia as eluent.

The fractions containing the pure product are pooled and evaporated to dryness.

4.3 g of N-1H-tetrazol-5-yl-[3-[5-bromo-(2-thienyl)]]-acrylamide trans isomer are obtained (yield 68.2%, M.P. 268° C., U.V. titre 99.7%).

| Analysis for $C_8H_6BrN_5OS$ | | |
|---|---|---|
| | % calculated | % found |
| C | 32.01 | 31.82 |
| H | 2.01 | 2.12 |
| N | 23.33 | 23.28 |
| S | 10.68 | 10.82 |

The following trans isomer compounds are prepared in a manner analogous to the aforesaid examples.

N-1H-TETRAZOL-5-YL-[3-[5-ETHYL-(2-THIENYL)]]-ACRYLAMIDE
N-1H-TETRAZOL-5-YL-[3-[4-CHLORO-(2-THIENYL)]]-ACRYLAMIDE
N-1H-TETRAZOL-5-YL-[3-[4-BUTYL-(2-THIENYL)]]-ACRYLAMIDE SODIUM SALT
N-1H-TETRAZOL-5-YL-[3-[3-CHLORO-(2-THIENYL)]]-ACRYLAMIDE
N-1H-TETRAZOL-5-YL-[3-[3-BROMO-(2-THIENYL)]]-ACRYLAMIDE SODIUM SALT.

EXAMPLE 15

N-1H-TETRAZOL-5-YL-[3-(3-THIENYL)] ACRYLAMIDE TRANS ISOMER (VAL 47-034)

10 g of 3-(3-thienyl) acrylic acid trans isomer (0.065 moles) (prepared as in Example 2), 6.695 g of 5-amino tetrazole monohydrate (0.065 moles) and 100 ml of anhydrous pyridine are placed in a dry apparatus kept under a stream of nitrogen.

The mixture temperature is raised to 60° C. and 18.72 g of dicyclohexylcarbodiimide (0.09 moles) dissolved in 30 ml of anhydrous pyridine are dripped in.

The reaction temperature is maintained at 60° C. for 2 hours, after which it is cooled and the precipitate which forms is filtered off through a Buchner funnel and then treated with an aqueous 5% sodium bicarbonate solution (500 ml), the resultant suspension is heated to 80° C. and the undissolved solid is filtered off under hot conditions through a folded filter.

The filtrate is cooled and acidified to pH 1 with concentrated HCl, the precipitate obtained being filtered off and dried.

12.3 g of N-1H-tetrazol-5-yl-[3-(3-thienyl)]-acrylamide trans isomer are obtained (yield 85.6%, M.P. 273°–274° C., U.V. titre 99.9%).

| Analysis for $C_8H_7N_5OS$ | | |
|---|---|---|
| | % calculated | % found |
| C | 43.42 | 43.53 |
| H | 3.19 | 3.09 |
| N | 31.65 | 31.52 |
| S | 14.49 | 14.31 |

EXAMPLE 16

N-1H-TETRAZOL-5-YL-[3-[5-ETHYL-(3-THIENYL)]-ACRYLAMIDE TRANS ISOMER 5 g of 3-(5-ethyl-3-thienyl) acrylic acid trans isomer (0.027 moles) (prepared as in Example 2), 2.78 g of 5-amino tetrazole monohydrate (0.027 moles) and 79 ml of anhydrous pyridine are placed in a previously dried apparatus kept under a stream of nitrogen.

2.295 g of silicon tetrachloride (0.0135 moles) are dripped into the solution. On completion of the addition, the mixture is left stirring at ambient temperature for 24 hours.

The reaction mixture is dripped into 500 ml of water-ice and stirred for 1 hour. A solid precipitates and is filtered off through a Buchner funnel, washed with water and crystallized with 112 ml of dimethylformamide.

After drying, 3.21 g of N-1H-tetrazol-5-yl-[3-[5-ethyl-(3-thienyl)]]-acrylamide trans isomer are obtained (yield 47.7%, M.P. 282°–284° C. dec., U.V. titre 99.6%).

| Analysis for $C_{10}H_{11}N_5OS$ | | |
|---|---|---|
| | % calculated | % found |
| C | 48.17 | 47.90 |
| H | 4.45 | 4.59 |
| N | 28.09 | 27.89 |
| S | 12.86 | 12.70 |

The following trans isomer compounds are prepared in a manner analogous to the aforesaid examples.

N-1H-TETRAZOL-5-YL-[3-[5-METHYL-(3-THIENYL)]]-ACRYLAMIDE
N-1H-TETRAZOL-5-YL-[3-[5-BROMO-(3-THIENYL)]]-ACRYLAMIDE
N-1H-TETRAZOL-5-YL-[3-[4-CHLORO-(3-THIENYL)]]-ACRYLAMIDE
N-1H-TETRAZOL-5-YL-[3-[4-PROPYL-(3-THIENYL)]]-ACRYLAMIDE
N-1H-TETRAZOL-5-YL-[3-[2-METHYL-(3-THIENYL)]]-ACRYLAMIDE
N-1H-TETRAZOL-5-YL-[3-[2-BROMO-(3-THIENYL)]]-ACRYLAMIDE.

EXAMPLE 17

N-1H-TETRAZOL-5-YL-[3-(2-PYRROLE)] ACRYLAMIDE TRANS ISOMER (VAL 47-078)

15 g of 3-(2-pyrrole) acrylic acid trans isomer (0.11 moles) (prepared as in Example 3) and 11.33 g of 5-amino tetrazole monohydrate (0.11 moles) are dissolved in 250 ml of anhydrous pyridine in a dry apparatus kept under a stream of nitrogen.

The mixture is heated to 60° C. and 22.71 g of dicyclohexylcarbodiimide (0.11 moles) dissolved in 22 ml of anhydrous pyridine are dripped in. The reaction temperature is maintained at 60° C. for 3 hours, after which the precipitate which forms is filtered off and the filtrate evaporated. The solid residue is ground with 163 ml of ethanol and left stirring for 4 hours.

It is filtered through a Buchner funnel and dried.

15.26 g of N-1H-tetrazol-5-yl-[3-(2-pyrrole)]-acrylamide trans isomer are obtained (yield 68%, M.P. 251°–253° C. dec.).

| Analysis for $C_8H_8N_6O$ | | |
|---|---|---|
| | % calculated | % found |
| C | 47.05 | 46.86 |
| H | 3.95 | 3.81 |
| N | 41.16 | 40.99 |

EXAMPLE 18

N-1H-TETRAZOL-5-YL-[3-(2-PYRIDYL)]-ACRYLAMIDE TRANS ISOMER (VAL 47-055)

A mixture composed of 5 g of 3-(2-pyridyl) acrylic acid trans isomer (0.033 moles) (prepared as in Example 4) and 10.70 g of 1,1'-carbonyldiimidazole (0.066 moles)

in 250 ml of anhydrous dimethylformamide is heated to 90° C. for 2 hours.

3.40 g of 5-amino tetrazole monohydrate (0.033 moles) dissolved in 45 ml of anhydrous dimethylformamide are dripped into this solution under stirring.

The resultant reaction mixture is heated to 100° C. for 2.5 hours.

On termination, the solvent is evaporated and the oily residue is treated hot with an aqueous 5% sodium bicarbonate solution (100 ml), the insoluble solid being removed by hot filtration through a folded filter.

The aqueous solution is cooled and acidified to pH 2 with 1:1 HCl. The precipitate which forms is filtered off through a Buchner funnel and dried.

2.8 g of N-1H-tetrazol-5-yl-[3-(2-pyridyl)]-acrylamide trans isomer are obtained (yield 38.63%, M.P. 275°-276° C.).

| Analysis for $C_9H_8N_6O$ | | |
|---|---|---|
| | % calculated | % found |
| C | 49.99 | 50.22 |
| H | 3.73 | 3.81 |
| N | 38.87 | 38.76 |

EXAMPLE 19

N-1H-TETRAZOL-5-YL-[3-[6-CHLORO-(2-PYRIDYL)]-ACRYLAMIDE SODIUM SALT TRANS ISOMER 7 g of 3-(6-chloro-2-pyridyl) acrylic acid trans isomer (0.038 moles) (prepared as in Example 4) are dissolved in 150 ml of anhydrous pyridine in a dry apparatus kept under a stream of nitrogen, and 3.91 g of 5-amino tetrazole monohydrate (0.038 moles) dissolved in 30 ml of anhydrous pyridine are added.

3.23 g of silicon tetrachloride (0.019 moles) are dripped into the mixture at ambient temperature and under stirring. On completion of the addition, the mixture is left at ambient temperature for 24 hours.

The reaction mixture is poured into 500 ml of water-ice and stirred for 3 hours. The solid which precipitates is filtered off through a Buchner funnel, washed with water, dried and chromatographed in a silica gel column using 9:1:0.5 acetone/water/acetic acid as eluent.

The fractions containing the pure product are pooled and evaporated to dryness. The solid obtained is taken up in an aqueous 5% sodium bicarbonate solution (75 ml) and heated to boiling. After cooling the solution in a freezer, a precipitate is obtained, which filtered off through a Buchner funnel and dried.

4.84 g of N-1H-tetrazol-5-yl-[3-[6-chloro-(2-pyridyl)]]-acrylamide sodium salt trans isomer are obtained (yield 46.7%, M.P.>300° C. dec.).

| Analysis for $C_9H_6N_6NaO$ | | |
|---|---|---|
| | % calculated | % found |
| C | 39.64 | 39.58 |
| H | 2.22 | 2.18 |
| N | 30.83 | 30.91 |

The following trans isomer compounds are prepared in a manner analogous to the aforesaid examples.

N-1H-TETRAZOL-5-YL-[3-[6-METHYL-(2-PYRIDYL)]]-ACRYLAMIDE

N-1H-TETRAZOL-5-YL-[3-[6-BENZYLOXY-(2-PYRIDYL)]]-ACRYLAMIDE

N-1H-TETRAZOL-5-YL-[3-[5-METHYL-(2-PYRIDYL)]]-ACRYLAMIDE SODIUM SALT

N-1H-TETRAZOL-5-YL-[3-[4-ISOPROPYL-(2-PYRIDYL)]]-ACRYLAMIDE

N-1H-TETRAZOL-5-YL-[3-[4-ETHYL-(2-PYRIDYL)]]-ACRYLAMIDE SODIUM SALT

N-1H-TETRAZOL-5-YL-[3-[4-BENZYLOXY-(2-PYRIDYL)]]-ACRYLAMIDE

N-1H-TETRAZOL-5-YL-[3-[4-BROMO-(2-PYRIDYL)]]-ACRYLAMIDE SODIUM SALT

N-1H-TETRAZOL-5-YL-[3-[3-METHYL-(2-PYRIDYL)]]-ACRYLAMIDE SODIUM SALT

N-1H-TETRAZOL-5-YL-[3-[3-CHLORO-(2-PYRIDYL)]]-ACRYLAMIDE

EXAMPLE 20

N-1H-TETRAZOL-5-YL-[3-(3-PYRIDYL)] ACRYLAMIDE TRANS ISOMER (VAL 47-017)

10 g of 3-(3-pyridyl) acrylic acid trans isomer (0.067 moles) (prepared as in Example 5), 6.9 g of 5-amino tetrazole monohydrate (0.067 moles) and 300 ml of anhydrous pyridine are placed in a dry apparatus kept under a stream of nitrogen.

13.80 g of dicyclohexylcarbodiimide (0.067 moles) dissolved in 13 ml of anhydrous pyridine are dripped into this mixture, the temperature of which is kept close to ambient during this addition.

The reaction temperature is maintained at the stated value for 6 hours, after which the precipitate which forms is filtered off, the filtrate is evaporated and the residue treated with an aqueous 5% sodium bicarbonate solution (500 ml).

The resultant suspension is heated to 85° C. and the undissolved solid is filtered off under hot conditions through a folded filter.

The filtrate is cooled and acidified to pH 3 with concentrated HCl.

The crystalline precipitate which separates is filtered off through a Buchner funnel, washed with water until neutral and dried.

5.78 g of N-1H-tetrazol-5-yl-[3-(3-pyridyl)]-acrylamide trans isomer are obtained (yield 39.9%, M.P. 294° C. dec.).

| Analysis for $C_9H_8N_6O$ | | |
|---|---|---|
| | % calculated | % found |
| C | 49.99 | 49.73 |
| H | 3.73 | 3.68 |
| N | 38.87 | 38.59 |

The following trans isomer compounds are prepared in a manner analogous to the aforesaid examples.

N-1H-TETRAZOL-5-YL-[3-[6-METHYL-(3-PYRIDYL)]]-ACRYLAMIDE

N-1H-TETRAZOL-5-YL-[3-[6-CHLORO-(3-PYRIDYL)]]-ACRYLAMIDE

N-1H-TETRAZOL-5-YL-[3-[6-BENZYLOXY-(3-PYRIDYL)]]-ACRYLAMIDE

N-1H-TETRAZOL-5-YL-[3-[5-METHYL-(3-PYRIDYL)]]-ACRYLAMIDE

N-1H-TETRAZOL-5-YL-[3-[4-ISOPROPYL-(3-PYRIDYL)]]-ACRYLAMIDE

N-1H-TETRAZOL-5-YL-[3-[4-ETHYL-(3-PYRIDYL)]]-ACRYLAMIDE

N-1H-TETRAZOL-5-YL-[3-[4-BROMO-(3-PYRIDYL)]]-ACRYLAMIDE

N-1H-TETRAZOL-5-YL-[3-[2-METHYL-(3-PYRIDYL)]]-ACRYLAMIDE
N-1H-TETRAZOL-5-YL-[3-[2-CHLORO-(3-PYRIDYL)]]-ACRYLAMIDE

EXAMPLE 21

N-1H-TETRAZOL-5-YL-[3-(2-PYRIDYL)]-ACRYLAMIDE TRANS ISOMER (VAL 47-042)

A mixture composed of 7 g of 3-(4-pyridyl) acrylic acid trans isomer (0.047 moles) (prepared as in Example 6) and 15.23 g of 1,1'-carbonylidiimidazole (0.094 moles) in 300 ml of anhydrous dimethylformamide is heated to 90° C. for 3 hours.

On termination of the heating, 4.84 g of 5-amino tetrazole monohydrate (0.047 moles) dissolved in 50 ml of anhydrous dimethylformamide are dripped into this solution and the mixture heated to 100° C. for 3 hours.

The solvent is then evaporated and the residual oil is dissolved in a hot aqueous 10% sodium bicarbonate solution (130 ml).

The solution is cooled and acidified with acetic acid until precipitation begins. The solid precipitate is filtered off through a Buchner funnel, dried and crystallized from dimethylformamide-water.

4.83 g of N-1H-tetrazol-5-yl-[3-(4-pyridyl)]-acrylamide trans isomer are obtained (yield 47.5%, M.P. 265°-266° C. dec., U.V. titre 99.6%).

| Analysis for $C_9H_8N_6O$ | | |
|---|---|---|
| | % calculated | % found |
| C | 49.99 | 49.90 |
| H | 3.73 | 3.66 |
| N | 38.87 | 38.92 |

The following trans isomer compounds are prepared in a manner analogous to the aforesaid examples.
N-1H-TETRAZOL-5-YL-[3-[2-METHYL-(4-PYRIDYL)]]-ACRYLAMIDE
N-1H-TETRAZOL-5-YL-[3-[2-ETHYL-(4-PYRIDYL)]]-ACRYLAMIDE
N-1H-TETRAZOL-5-YL-[3-[3-METHYL-(4-PYRIDYL)]]-ACRYLAMIDE
N-1H-TETRAZOL-5-YL-[3-[2-BENZYLOXY-(4-PYRIDYL)]]-ACRYLAMIDE
N-1H-TETRAZOL-5-YL-[3-[2-ACETOXY-(4-PYRIDYL)]]-ACRYLAMIDE
N-1H-TETRAZOL-5-YL-[3-[2-CHLORO-(4-PYRIDYL)]]-ACRYLAMIDE
N-1H-TETRAZOL-5-YL-[3-[3-CHLORO-(4-PYRIDYL)]]-ACRYLAMIDE.

EXAMPLE 22

3-(2-FURYL) ACRYLOYL CHLORIDE TRANS ISOMER 15 g of 3-(2-furyl) acrylic acid trans isomer (0.11 moles) (prepared in accordance with Example 7) are mixed with 19.63 g of freshly distilled thionyl chloride (0.165 moles) and 70 ml of anhydrous benzene in a dry apparatus kept under a stream of nitrogen.

The mixture is heated under reflux for 7 hours, after which it is cooled and the excess thionyl chloride is distilled under reduced pressure.

The residue is washed several times with N-hexane and the solvent completely evaporated to obtain a dense oil which solidifies completely at low temperature.

14.32 g of 3-(2-furyl) acryloyl chloride trans isomer are obtained (yield 83%, Cl⁻ titre 98.9%).

| Analysis for $C_7H_5ClO_2$ | | |
|---|---|---|
| | % calcualted | % found |
| C | 53.70 | 53.61 |
| H | 3.22 | 3.40 |
| Cl | 22.65 | 22.77 |

N-1H-TETRAZOL-5-YL-[3-(2-FURYL)] ACRYLAMIDE TRANS ISOMER (VAL 47-010)

5 g of 5-aminotetrazole monohydrate (0.048 g) are placed in a suitable apparatus and are hot-dissolved in 145 ml of tetrahydrofuran and 7.3 ml of water.

3.75 g of 3-(2-furyl) acryloyl chloride trans isomer (0.024 moles) dissolved in 50 ml of tetrahydrofuran are dripped into the obtained solution, after which the mixture is refluxed for 3 hours. The reaction mixture is then cooled, 100 ml of water are added and the system is placed in a refrigerator overnight.

The solid which separates is filtered off through a Buchner funnel and treated with an aqueous 5% sodium bicarbonate solution (400 ml) and kept stirring at 80° C. for 1 hour.

The solution obtained is cooled and acidified to pH 1 with concentrated HCl.

The precipitated solid is filtered off through a Buchner funnel, dried and chromatographed in a silica gel column using 6.5:2.5:0.4 chloroform/methanol/water as eluent.

The fractions containing the pure product are pooled and evaporated to dryness.

3.58 g of N-1H-tetrazol-5-yl-[3-(2-furyl)]-acrylamide trans isomer are obtained (yield 72.7%, M.P. 287°-289° C.).

| Analysis for $C_8H_7NO_2$ | | |
|---|---|---|
| | % calculated | % found |
| C | 46.83 | 46.56 |
| H | 3.44 | 3.28 |
| N | 34.13 | 34.33 |

EXAMPLE 23

N-1H-TETRAZOL-5-YL-[3-[5-METHYL-(2-FURYL)]] ACRYLAMIDE TRANS ISOMER (VAL 47-073)

12.58 g of 3-(5-methyl-2-furyl) acrylic acid trans isomer (0.0827 moles) (prepared as in Example 8) dissolved in 200 ml of tetrahydrofuran and 9.6 g of 5-amino tetrazole monohydrate (0.093 moles) dissolved in 282 ml of tetrahydrofuran and 14.3 ml of water are placed in a flask.

The mixture temperature is raised to 60° C. and 18.72 g of dicyclohexylcarbodiimide (0.093 moles) are added in a single solution.

The reaction temperature is maintained at 60° C. for 4 hours, after which the solid precipitate which forms is filtered off through a Buchner funnel and the filtrate evaporated to dryness. The residue is taken up in an aqueous 5% sodium bicarbonate solution (1 liter), the resultant suspension is heated to 80° C. and the undissolved solid is filtered off under hot conditions through a folded filter.

The filtrate is cooled and acidified to pH 1 with concentrated hydrochloric acid, the precipitate obtained being filtered off and dried.

13.2 g of N-1H-tetrazol-5-yl-[3-[5-methyl-(2-furyl)]]-acrylamide trans isomer are obtained (yield 72.8%, M.P. 264°–265° C.).

| Analysis for $C_9H_9N_5O_2$ | | |
|---|---|---|
| | % calculated | % found |
| C | 49.31 | 49.51 |
| H | 4.14 | 4.23 |
| N | 31.95 | 31.98 |

The following trans isomer compounds are prepared in a manner analogous to the aforesaid examples.

N-1H-TETRAZOL-5-YL-[3-[5-ACETOXYMETH-YL-(2-FURYL)]]-ACRYLAMIDE

N-1H-TETRAZOL-5-YL-[3-[5-BENZYLOXY-(2-FURYL)]]-ACRYLAMIDE.

EXAMPLE 24

N-1H-TETRAZOL-5-YL-[3-(3-INDOLYL)] ACRYLAMIDE TRANS ISOMER (VAL 47-022)

10 g of 3-(3-indolyl) acrylic acid trans isomer (0.053 moles) (prepared as in Example 9), 6.1 g of 5-amino tetrazole monohydrate (0.059 moles) and 100 ml of anhydrous pyridine are placed in a dry apparatus kept under a stream of nitrogen.

12.17 g of dicyclohexylcarbodiimide (0.059 moles) dissolved in 12 ml of anhydrous pyridine are dripped into this mixture, the temperature of which is kept close to ambient during this addition.

The reaction mixture is maintained at the stated temperature for 1 hour after which the precipitated solid which forms is filtered off, the filtrate is evaporated and the residue treated with an aqueous 5% sodium bicarbonate solution (500 ml).

The resultant suspension is heated to 85° C. and the undissolved solid is filtered off through a folded filter.

The filtrate is cooled and acidified to pH 1 with concentrated hydrochloric acid. The crystalline precipitate which separates is filtered off through a Buchner funnel, washed with water until neutral and dried. 6.5 g of N-1H-tetrazol-5-yl-[3-(3-indolyl)]-acrylamide trans isomer are obtained (yield 48.3%, M.P. 281° C. dec.).

| Analysis for $C_{12}H_{10}N_6O$ | | |
|---|---|---|
| | % calculated | % found |
| C | 56.68 | 56.81 |
| H | 3.96 | 3.88 |
| N | 33.05 | 33.19 |

EXAMPLE 25

N-1H-TETRAZOL-5-YL-[3-(2-QUINOLYL)] ACRYLAMIDE TRANS ISOMER 10 g of 3-(2-quinolyl) acrylic acid trans isomer (0.05 moles) (prepared as in Example 10) dissolved in 30 ml of anhydrous pyridine and 5.15 g of 5-amino tetrazole monohydrate (0.05 moles) dissolved in 65 ml of anhydrous pyridine are placed in a dry apparatus kept under a stream of nitrogen.

The mixture temperature is raised to 60° C. and 10.32 g of dicyclohexylcarbodiimide (0.05 moles) dissolved in 10 ml of anhydrous pyridine are dripped in.

The reaction flask is maintained at 60° C. for 3 hours, after which it is cooled and the precipitate which forms is filtered off and the filtrate evaporated to dryness.

The solid residue is treated with an aqueous 5% sodium bicarbonate solution (500 ml). The mixture is heated to 80° C. and kept at this temperature for one hour and a half. The solution is then cooled and acidified with concentrated hydrochloric acid until precipitation begins.

The precipitate obtained is filtered off through a Buchner funnel, dried and crystallized with 52 ml of dimethylformamide.

7.68 g of N-1H-tetrazol-5-yl-[3-(2-quinolyl)]-acrylamide trans isomer are obtained (yield 57.74%, M.P. 281° C. dec.).

| Analysis for $C_{13}H_{10}N_6O$ | | |
|---|---|---|
| | % calculated | % found |
| C | 58.64 | 58.50 |
| H | 3.78 | 3.64 |
| N | 31.57 | 31.39 |

EXAMPLE 26

N-1H-TETRAZOL-5-YL-[3-(4-QUINOLYL)] ACRYLAMIDE TRANS ISOMER (VAL 47-067)

8 g of 3-(4-quinolyl) acrylic acid trans isomer (0.04 moles) (prepared as in Example 11), 5.15 g of 5-amino tetrazole monohydrate (0.05 moles) and 200 ml of anhydrous pyridine are placed in a dry apparatus kept under a stream of nitrogen.

11.23 g of dicyclohexylcarbodiimide dissolved in 20 ml of anhydrous pyridine are dripped into this solution. When the addition is complete, the mixture is left at ambient temperature under stirring for 1 hour.

The precipitate which forms during stirring is filtered off through a Buchner funnel and taken up in a boiling aqueous 5% sodium bicarbonate solution (600 ml), and the undissolved solid is filtered off under hot conditions through a folded filter.

The filtrate is cooled and acidified until the precipitate has totally formed, this being filtered off through a Buchner funnel and dried.

5.809 g of N-1H-tetrazol-5-yl-[3-(2-quinolyl)]-acrylamide trans isomer are obtained (yield 54.3%, M.P. 265°–266° C.).

| Analysis for $C_{13}H_{10}N_6O$ | | |
|---|---|---|
| | % calculated | % found |
| C | 58.64 | 58.46 |
| H | 3.78 | 3.90 |
| N | 31.57 | 31 43 |

EXAMPLE 27

A METHOD 3-(5-METHYL-2-THIENYL) ACRYLIC ACID METHYL ESTER TRANS ISOMER 30.24 g of 5-methyl-2-thiophene carboxaldehyde (0.24 moles) dissolved in 150 ml of anhydrous pyridine and 5 drops of piperidine are placed in a previously dried flask fitted with a mechanical stirrer.

28.08 g of malonic acid monomethyl ester (0.24 moles) dissolved in 20 ml of anhydrous pyridine are dripped into the reaction mixture at ambient temperature.

The reaction mixture is placed in the dark under stirring for 3 hours and then left standing for 15 hours. After this period it is heated to 80° C. until the reaction has gone to completion. The solvent is evaporated and the solid obtained is crystallized with 80 ml of ethyl acetate.

40.61 g of 3-(5-methyl-2-thienyl) acrylic acid methyl ester trans isomer are obtained (yield 93%, M.P. 59°-60° C.).

| Analysis for $C_9H_{10}O_2S$ | | |
|---|---|---|
| | % calculated | % found |
| C | 59.31 | 59.10 |
| H | 5.53 | 5.42 |
| S | 17.59 | 17.44 |

3-(5-METHYL-2-THIENYL) ACRYLIC ACID METHYL ESTER CIS ISOMER 30 g of 3-(5-methyl-2-thienyl) acrylic acid methyl ester trans isomer (0.165 moles) are dissolved in 190 ml of acetonitrile, placed in a suitable apparatus and irradiated for 140 minutes at ambient temperature with a high pressure mercury lamp.

On termination of the reaction, the solvent is evaporated and the residual oil is chromatographed in a silica gel column using 5.5:4.5 methylene chloride/N-hexane as eluent.

The fractions containing the pure product are pooled and evaporated to dryness.

13.2 g of 3-(5-methyl-2-thienyl) acrylic acid methyl ester cis isomer are obtained (yield 44%, B.P. at atmospheric pressure 250° C.).

| Analysis of $C_9H_{10}O_2S$ | | |
|---|---|---|
| | % calculated | % found |
| C | 59.31 | 59.58 |
| H | 5.53 | 5.44 |
| S | 17.59 | 17.63 |

B METHOD

5-METHYL-2-THIOPHENE-CARBONYL-CHLORIDE 50 g 5-methyl-2-thiophene carboxylic acid (0.352 moles) are mixed, in a dry apparatus under a stream of nitrogen, with 125.6 g of freshly distilled thionyl chloride (1.055 moles). The apparatus is heated under reflux for 7 hrs. After cooling, the excess thionyl chloride is distilled off under the suction of a water pump, while the residue is distilled under high vacuum (e.g. at 73°-74° C. under $10^{-1}$ mmHg).

54 g 5-methyl-2-thiophen-carbonyl chloride are obtained. (yield: 95.6%; Cl− 99.7%)

| Analysis for $C_6H_5ClOS$ | | |
|---|---|---|
| | % calculated | % found |
| C | 44.86 | 44.79 |
| H | 3.14 | 2.99 |
| S | 19.96 | 19.81 |

3-(5-METHYL-2-THIENYL) PROPIOLIC ACID METHYL ESTER 212 g methyl-(triphenylphosphoranilidene) acetate (0.635 moles) are suspended in 1580 anhydrous benzene, operating in a dry apparatus under a stream of nitrogen, under vigorous stirring.

There are added dropwise 51 g 5-methyl-2-thiophen-carbonyl chloride (0.318 moles) in 370 ml anhydrous benzene so as to keep the temperature of the reaction mixture around 25° C. At the end of the addition, the stirring is continued to complete the reaction.

The undissolved solid is filtered on a Buchner funnel and the filtrate is evaporated. 145,5 g phosphoranyl intermediate are obtained.

This amount is introduced into a perfectly dry apparatus and a 7 mmHg vacuum is applied. The kettle is then heated until the solid contained is completely melted.

The distillation of the desired product is terminated after about 3 hrs. The thus obtained oil is then purified by flash-chromatography on a silica gel column using $CHCl_3$ as eluent.

The fractions containing the pure product are put together and heated to dryness.

45 g 3-(5-methyl-2-thienyl) propiolic acid methyl ester are obtained. (yield: 78.6%; b.p. 7 mmHg: 152° C.)

| Analysis for $C_9H_8O_2S$ | | |
|---|---|---|
| | % calculated | % found |
| C | 59.98 | 60.03 |
| H | 4.47 | 4.61 |
| S | 17.79 | 17.54 |

3-(5-METHYL-2-THIENYL) ACRYLIC ACID METHYL ESTER CIS ISOMER 5 g (0.05 mols) 3-(5-methyl-2-thienyl) propiolic acid methyl ester dissolved in 80 ml anhydrous pyridine and with the addition of 1.08 g 5% palladium on barium sulphate are introduced into a PARR apparatus for hydrogenation under pressure (15 psi=1.02 atm.).

Once the hydrogen absorption is over, the catalyst is filtered off and the mixture is distilled to dryness.

The residual oil is purified by chromatography on a silica gel column, eluent methylene chloride/n-hexane 5,5:4. The fractions containing the pure product are put together and heated to dryness.

7.3 g 3-(5-methyl-2-thienyl) acrylic acid methyl ester, CIS isomer are obtained. (yield: 80%; b.p. (normal pressure): 250° C.)

| Analysis for $C_9H_{10}O_2S$ | | |
|---|---|---|
| | % calculated | % found |
| C | 59.31 | 59.29 |
| H | 5.53 | 5.46 |
| S | 17.59 | 17.70 |

3-(5-METHYL-2-THIENYL) ACRYLIC ACID CIS ISOMER 7.09 g of 3-(5-methyl-2-thienyl) acrylic acid methyl ester cis isomer (0.039 moles) (preparation according to the method A or B) dissolved in 1200 ml of acetonitrile and 27.5 g of sodium hydroxide (0.687 moles) dissolved in 710 ml of water are placed in a flask.

The mixture is heated to 65° C. until the reactants disappear.

The reaction is extinguished by evaporating the solvent, the solid being taken up with water and acidifying to pH 1 with concentrated hydrochloric acid. The precipitate which forms is filtered off through a Buchner funnel and dried. 4.5 g of 3-(5-methyl-2-thienyl) acrylic acid cis isomer are obtained (yield 68.7%, M.P. 118°–120° C., H+ titre 98.2%).

| Analysis for $C_8H_8O_2S$ | | |
|---|---|---|
| | % calculated | % found |
| C | 57.12 | 56.98 |
| H | 4.79 | 4.83 |
| S | 19.06 | 19.14 |

EXAMPLE 28

A METHOD

3-(5-METHYL-2-FURYL) ACRYLIC ACID ETHYL ESTER TRANS ISOMER 43.25 g of 5-methyl-furfural (0.39 moles) dissolved in 86 ml of anhydrous pyridine and 5 drops of piperidine are placed in an apparatus kept under a stream of nitrogen.

51.9 of malonic acid monomethyl ester (0.39 moles) dissolved in 30 ml of anhydrous pyridine are dripped into the reaction mixture at ambient temperature.

The reaction mixture is placed in the dark under stirring for 3 hours and then left standing for 15 hours. After this period it is heated to 80° C. for 3 hours.

The solvent is evaporated and the residue is distilled under vacuum with a mechanical pump.

The distillate fractions containing the pure product are pooled.

59 g of 3-(5-methyl-2-furyl) acrylic acid ethyl ester trans isomer are obtained (yield 83%, B.P. 118°–120° C. at 8 mmHg).

| Analysis for $C_{10}H_{12}O_3$ | | |
|---|---|---|
| | % calculated | % found |
| C | 66.65 | 66.73 |
| H | 6.71 | 6.82 |

3-(5-METHYL-2-FURYL) ACRYLIC ACID ETHYL ESTER CIS ISOMER 40 g of 3-(5-methyl-2-furyl) acrylic acid ethyl ester trans isomer (0.22 moles) are dissolved in 200 ml of acetonitrile, placed in a suitable apparatus and irradiated for 30 minutes at ambient temperature with a high pressure mercury lamp.

On termination of the reaction, the solvent is evaporated and the residual oil is distilled under vacuum using a mechanical pump.

The distillate fractions containing the pure product are pooled.

17.3 g of 3-(5-methyl-2-furyl) acrylic acid ethyl ester cis isomer are obtained (yield 86.5% B.P. 147°–148° C. at 8 mmHg).

| Analysis for $C_{10}H_{12}O_3$ | | |
|---|---|---|
| | % calculated | % found |
| C | 66.65 | 66.70 |
| H | 6.71 | 6.69 |

B METHOD

5-METHYL-2-FURYL-CARBONYL-CHLORIDE 63 g 5-methyl-2-furyl-carboxylic acid (0.5 moles) are mixed with 178.5 g (1.5 moles) freshly distilled thionyl chloride in a perfectly dry apparatus in a nitrogen atmosphere.

The mixture is heated under reflux for 6 hrs. After cooling, the excess thionyl chloride is distilled under water-pump suction while the residue is distilled under high vacuum.

70.8 g 5-methyl-2-furyl-carbonylchloride are obtained. (yield: 98%; Cl−: 99.87%)

| Analysis for $C_6H_5ClO_2$ | | |
|---|---|---|
| | % calculated | % found |
| C | 49.85 | 49.78 |
| H | 3.49 | 3.60 |
| Cl | 24.53 | 24.49 |

3-(5-METHYL-2-FURYL) PROPIOLIC ACID ETHYL ESTER 208.8 g ethyl-(triphenyl phosphoranilidene) acetate (0.6 moles) are suspended in 1500 ml anhydrous freshly distilled benzene in a anhydrous apparatus in a nitrogen atmosphere; 43.35 g (0.3 moles) 5-methyl-2-furyl-carbonyl chloride in 300 ml anhydrous benzene are added dropwise under vigorous stirring. The addition is controlled so as to keep the reaction mixture at a temperature around 25° C.

Once the addition is terminated, stirring is continued to complete the reaction.

The undissolved solid is filtered on a Buchner funnel, while the filtrate is evaporated. 130 g phosphoranic intermediate are obtained.

This amount is introduced in a perfectly dry distillation apparatus. Operating under a residual pressure of 7 mmHg the kettle is heated until complete melting of the solid contents.

The distillation of the desired product is terminated after about 2 hrs.

The thus obtained oil is purified by chromatography on a silica gel column employing $CH_2Cl_2$/n-hexane as eluent.

The fractions containing the pure product are put together and evaporated.

45.29 g 3-(5-methyl-2-furyl) propiolic acid ethyl ester are obtained.

(yield 85.0%).

| Analysis for $C_{10}H_{10}O_3$ | | |
|---|---|---|
| | % calculated | % found |
| C | 67.40 | 67.38 |
| H | 5.66 | 5.55 |

3-(5-METHYL-2-FURYL) ACRYLIC ACID ETHYL ESTER CIS ISOMER 35.6 g 3-(5-methyl-2-furyl) propiolic acid ethyl ester (0.2 moles) dissolved in 500 ml anhydrous pyridine, with the addition of 3.5 g 5% palladium on barium sulphate are introduced into a PARR apparatus for hydrogenation under pressure (15 psi=0.2 atm).

Once the hydrogen absorption is over, the catalyst is filtered off and the mixture is distilled to dryness.

The residual oil is purified by chromatography on a silica gel column employing $CHCl_3$/n-hexane 4:6 as eluent.

The fractions containing the pure product are put together and distilled to dryness.

33.12 g 3-(5-methyl-2-furyl) acrylic acid ethyl ester CIS isomer are obtained.

(yield: 92.0%).

| Analysis for $C_{10}H_{12}O_3$ | | |
|---|---|---|
| | % calculated | % found |
| C | 66.65 | 66.79 |
| H | 6.71 | 6.83 |

3-(5-METHYL-2-FURYL) ACRYLIC ACID CIS ISOMER 17.3 g of 3-(5-methyl-2-furyl) acrylic acid ethyl ester cis isomer (0.096 moles) prepared according to the method A or B) dissolved in a mixture consisting of 11.66 g of sodium hydroxide (0.29 moles), 700 ml of ethanol and 250 ml of water are placed in a flask.

The mixture is heated under reflux with strong stirring until the starting ester disappears.

The reaction is extinguished by evaporating the solvent, the solid residue being taken up in 400 ml water and acidifying to pH 1 with concentrated hydrochloric acid.

The precipitate which forms is filtered off through a Buchner funnel and dried.

12.46 g of 3-(5-methyl-2-furyl) acrylic acid cis isomer are obtained (yield 85.4%, M.P. 148°–149° C., H+ titre 98.4%).

| Analysis for $C_8H_8O_3$ | | |
|---|---|---|
| | % calculated | % found |
| C | 63.15 | 63.21 |
| H | 5.30 | 5.33 |

EXAMPLE 29

N-1H-TETRAZOL-5-YL-[3-[5-METHYL-(2-THIENYL)]] ACRYLAMIDE CIS ISOMER (VAL 47-005 CIS)

4.5 g of 3-(5-methyl-2-thienyl) acrylic acid cis isomer (0.027 moles) (prepared as in Example 27) dissolved in 96 ml of tetrahydrofuran, 3.11 g of 5-amino tetrazole monohydrate (0.03 moles) dissolved in 90.7 ml of tetrahydrofuran and 4.6 ml of water are placed in a flask.

The mixture temperature is raised to 60° C. and 8.46 g of dicyclohexylcarboditimide (0.041 moles) dissolved in 25 ml of tetrahydrofuran are dripped in.

The reaction temperature is maintained at 60° C. for 4 hours, after which the solvent is evaporated and the residue is treated with an aqueous 5% sodium bicarbonate solution (200 ml), the resultant suspension is heated to 80° C. and the undissolved solid is filtered off under hot conditions through a folded filter. The filtrate is cooled and acidified to pH 1 with concentrated hydrochloric acid, the precipitate obtained being filtered off and dried.

3.976 g of N-1H-tetrazol-5-yl-[3-[5-methyl-(2-thienyl)]]acrylamide cis isomer are obtained (yield 62.96%, M.P. 260° C. dec.).

| Analysis for $C_9H_9N_5OS$ | | |
|---|---|---|
| | % calculated | % found |
| C | 45.94 | 46.12 |
| H | 3.85 | 4.03 |
| N | 29.77 | 29.59 |
| S | 13.63 | 13.54 |

EXAMPLE 30

N-1H-TETRAZOL-5-YL-[3-[5-METHYL-(2-FURYL)]] ACRYLAMIDE CIS ISOMER (VAL 47-073CIS)

2.47 g of 3-(5-methyl-2-furyl) acrylic acid cis isomer (0.016 moles) (prepared as in Example 28) dissolved in 40 ml of tetrahydrofuran and 1.87 g of 5-amino tetrazole monohydrate (0.018 moles) dissolved in 54.3 ml of tetrahydrofuran and 2.75 ml of water are placed in a flask.

The mixture temperature is raised to 60° C. and 3.71 g of dicyclohexylcarbodiimide (0.018 moles) are added in a single solution.

The reaction temperature is maintained at 60° C. for 5 hours, after which the solid precipitate is removed by filtration through a Buchner funnel and the filtrate is evaporated to dryness.

The residue is taken up in an aqueous 5% sodium bicarbonate solution (200 ml), the resultant suspension is heated to 80° C. and the undissolved solid is filtered off under hot conditions through a folded filter.

The filtrate is cooled and acidified to pH 1 with concentrated hydrochloric acid, the precipitate obtained being filtered off and dried.

2.35 g of N-1H-tetrazol-5-yl-[3-[5-methyl-(2-furyl)]]-acrylamide cis isomer are obtained (yield 67%, M.P. 258°–259° C. dec.).

| Analysis for $C_9H_9N_5O_2$ | | |
|---|---|---|
| | % calculated | % found |
| C | 49.31 | 49.42 |
| H | 4.14 | 4.15 |
| N | 31.95 | 31.88 |

The following cis isomer compounds are prepared in a manner analogous to the aforesaid examples.

N-1H-TETRAZOL-5-YL-[3-(2-PYRROLE)]-ACRYLAMIDE CIS ISOMER

N-1H-TETRAZOL-5-YL-[3-(2-PYRIDYL)]-ACRYLAMIDE CIS ISOMER

N-1H-TETRAZOL-5-YL-[3-(3-PYRIDYL)]-ACRYLAMIDE CIS ISOMER

N-1H-TETRAZOL-5-YL-[3-(4-PYRIDYL)]-ACRYLAMIDE CIS ISOMER

N-1H-TETRAZOL-5-YL-[3-(2-FURYL)]-ACRYLAMIDE CIS ISOMER

N-1H-TETRAZOL-5-YL-[3-(3-INDOLYL)]-ACRYLAMIDE CIS ISOMER

N-1H-TETRAZOL-5-YL-[3-(2-QUINOLYL)]-
ACRYLAMIDE CIS ISOMER
N-1H-TETRAZOL-5-YL-[3-(4-QUINOLYL)]-
ACRYLAMIDE CIS ISOMER
N-1H-TETRAZOL-5-YL-3-(2-THIENYL)-
ACRYLAMIDE CIS ISOMER

PHARMACOLOGICAL TRIALS

The derivatives of general formula (I) according to the present invention were subjected to considerable experimentation in vivo to determine their antiallergic activity.

The pharmacological test used was the passive cutaneous anaphylaxis test (PCA test) on the rat in accordance with the method described by Goose J. and Blair A. M. J. M. (Immunology, 16, 749, 1969).

The serum, obtained from rats actively sensitized with ovalbumin (antigen) and suitably diluted, was injected intradermically into the shaven back of male Sprague Dawley rats (2 wheals per rat).

The rats were treated intravenously after 24 hours with a solution of ovalbumin and Evans blue. Thirty minutes later they were killed and the diameter and intensity of the blue ring formed at the site of the intradermic injection were measured.

For each treated group (5 per group) the % inhibition was then calculated with respect to the control group. Where possible, the $ED_{50}$ was calculated for each compound, i.e. the dose able to determine a 50% inhibition, together with the confidence limits (P=0.05).

The pharmacological screening was effected by administering the compounds of the present invention intravenously and orally.

For intravenous administration (2 ml/kg), those compounds in which $R_1 = H$ (see formula I) were dissolved in an aqueous 1% $NaHCO_3$ solution whereas for oral administration (4 ml/Kg) they were either suspended in 0.5% carboxymethylcellulose or dissolved in an aqueous 3% $NaHCO_3$ solution.

Table 1 shows the results obtained when the compounds were administered intravenously at doses of between 0.1 and 30 mg/kg just before the challenge with the antigen. The same table also shows the results with DSCG used as the reference compound for intravenous administration.

As can be seen, the compounds show a potent dose-dependent effect in inhibiting passive cutaneous anaphylaxis in the rat, similar to that obtained with DSCG.

Specifically, the $ED_{50}$ values for VAL 47-017, VAL 47-067 and VAL 47-005 cis are 0.36, 0.35 and 0.89 mg/Kg/iv respectively, whereas that for DSCG under our experimental conditions was 0.52 mg/Kg/iv.

It can also be seen that the compound VAL 47-005 cis in which the double bond of the alkenyl chain (see formula I) is in cis configuration, has an activity about 3 times greater than its trans isomer (VAL 47-005). The $ED_{50}$ for VAL 47-005 cis is 0.89 mg/kg/i.v. whereas for VAL 47-005 it is 2.99 mg/kg/i.v.

The results of the pharmacological screening in the PCA test on the rat for oral administration at doses of between 0.3 and 30 mg/kg/os administered 5 minutes before the challenge with the antigen are shown in Table 2.

The table also shows the results obtained with Tranilast used as oral administration reference standard, and with the product TA 57-07 synthesized in our laboratories.

The Tranilast (100 mg/kg/os) was administered 15 minutes before the challenge because the time-response curve (see Table 3) shows that the peak effect under our experimental conditions was in fact at 15 minutes.

The products of the present invention show a dose-dependent activity in inhibiting passive cutaneous anaphylaxis in the rat which is greater to the extent of even three orders of magnitude than that of Tranilast ($ED_{50}$=115.1 mg/kg/os)

The most active compounds, i.e. those for which it was possible to calculate an $ED_{50}$ taking account of the fact that the maximum dose administered in this screening was 30 mg/kg/os, have an $ED_{50}$ of between 0.78 mg/kg/os (VAL 47-005 cis) and 12.37 mg/Kg/os (VAL 47-010).

The compounds VAL 47-005 cis, VAL 47-073 and VAL 47-073 cis ($ED_{50}$ 0.78, 0.92, 1.26 mg/kg/os respectively) were analogous, in terms of potency of effect, to TA 57-07 which, under our experimental conditions and when administered 5 minutes before the challenge, has an $ED_{50}$ of 0.93 mg/kg/os with confidence limits (P=0.05) of 0.61 and 1.42 mg/kg/os.

It can also be seen that the most active compounds on oral administration have a bioavailability higher than the compound TA 57-07. In this respect, the ratios of the $ED_{50}$ values obtained after oral administration (5 minutes before the challenge) to those after i.v. administration (immediately before the challenge) are:

|  | $ED_{50}$ OS/$ED_{50}$ iv |
|---|---|
| TA 57-07 | 15.76 |
| VAL 47-005 | 4.13 |
| VAL 47-005 cis | 0.88 |
| VAL 47-010 | 3.95 |
| VAL 47-073 | 0.29 |
| VAL 47-073 cis | 0.22 |
| VAL 47-055 | 5.15 |

(N.B. The $ED_{50}$ of the compound TA 57-07 for intravenous administration was 0.059 mg/kg/iv under our experimental conditions).

In order to evaluate the duration of the antiallergic effect after oral administration, a reliably active dose of the compounds of the present invention was administered 5, 15, 30, 60 and 120 minutes before the challenge with the antigen (see Table 3).

The same table also shows the results obtained with Tranilast and with the compound TA 57-07.

Analyzing the results shown in Table 3, it can be seen that most of the tested compounds have their maximum pharmacological effect when administered orally 5 minutes before the challenge with the antigen, in contrast to Tranilast the peak effect of which, under our experimental conditions, is obtained if administered 15 minutes before. When Tranilast is administered 5 minutes before the challenge with the antigen at a dose of 100 mg/kg/os it determines an inhibition of 17.9%.

Acute toxicity was evaluated in the mouse by administering the compounds orally at scalar doses to a maximum of 1000 mg/kg to evaluate the 50% lethal dose ($LD_{50}$). The compounds were administered in carboxymethylcellulose (0.5%) in a volume of 0.2 ml/kg to male mice (Swiss stock) of average weight 20 g.

The $LD_{50}$ of the compounds of the present invention for oral administration in the mouse was certainly greater than 1000 mg/kg (maximum dose administered) in that up to this dose no lethal effects which would have enabled it to be calculated were observed.

An analysis of the data given in Table 4 shows inter alia that the reference compounds Tranilast and TA 57-07 at a dose of 1000 mg/kg/os determine a mortality of 87.5% and 50% respectively. In contrast, at the same dose of 1000 mg/kg the compounds of the present invention show no mortality with the exception of the compounds VAL 47-034, VAL 47-010, VAL 47-067 and VAL 47-073 cis which determine a mortality of between 12.5 and 25%. The most active compounds in the PCA test with oral administration (VAL 47-005 cis, VAL 47-073 and VAL 47-073 cis) do not determine any toxic effect at the stated dose, the only exception being VAL 47-073 cis, which shows a mortality of 12.5%.

The aforesaid results clearly show that the derivatives of the invention have high antiallergic activity not only for intravenous administration but also for oral administration at doses which are only slightly greater and sometimes less than those used intravenously, and with only 5 minutes of pretreatment.

When compared with Tranilast and with the compound TA 57-07, these are found to be less bioavailable when administered orally than the compounds of the present invention. Tranilast has also proved less active by at least one order of magnitude.

The compounds of the present invention, for oral administration in the mouse, show less toxicity than Tranilast and TA 57-07, this indicating a higher therapeutic index for equal pharmacological activity.

TABLE 1

ANTIALLERGIC ACTIVITY IN THE RAT
PCA Test
Intravenous administration
immediately before challenge with antigen

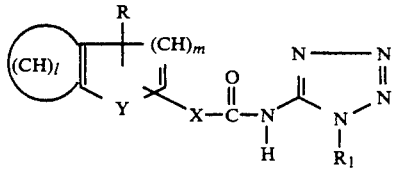

| | | | | | | | mg/kg/iv | | | | | | |
|---|---|---|---|---|---|---|---|---|---|---|---|---|---|
| | | | | | | 0.1 | 0.3 | 1 | 3 | 10 | 30 | $ED_{50}$ | (conf. lim) |
| COMPOUND | Y | m | X | R | $R_1$ | l | | inhibition (%) | | | | (mg/kg/iv) | P = 0.05 |
| D.S.C.G. | ... | ... | ... | ... | ... | ... | 28.1 | 33.6 | 70.0 | 100 | — | — | 0.52 | (0.47–0.83) |
| VAL 47-024 | S | 1 | 2-(CH=CH) | H | H | 0 | — | — | 18.1 | 64.9 | 100 | — | 2.29 | (1.68–3.14) |
| VAL 47-005 | S | 1 | 2-(CH=CH) | 5-$CH_3$ | H | 0 | — | — | 20.3 | 43.4 | 89.4 | — | 2.99 | (2.12–4.24) |
| VAL 47-005Na | S | 1 | 2-(CH=CH) | 5-$CH_3$ | Na | 0 | — | — | 16.5 | 40.7 | 78.0 | — | 3.74 | (2.89–4.85) |
| VAL 47-005cis | S | 1 | 2-(CH=CH) | 5-$CH_3$ | H | 0 | — | 18.0 | 54.6 | 82.9 | — | — | 0.89 | (0.56–1.42) |
| VAL 47-008 | S | 1 | 2-(CH=CH) | 5-Br | H | 0 | — | — | 0 | 8.6 | 31.9 | 82.3 | 12.84 | (10.08–16.36) |
| VAL 47-034 | S | 1 | 3-(CH=CH) | H | H | 0 | — | — | 1.3 | 48.6 | 63.5 | — | 4.74 | (2.97–7.57) |
| VAL 47-010 | O | 1 | 2(CH=CH) | H | H | 0 | — | — | 29.0 | 40.2 | 84.1 | 95.3 | 3.13 | (2.05–4.77) |
| VAL 47-073 | O | 1 | 2-(CH=CH) | 5-$CH_3$ | H | 0 | — | — | 3.4 | 50.7 | 95.1 | — | 3.13 | (2.35–4.17) |
| VAL 47-073cis | O | 1 | 2(CH=CH) | 5-$CH_3$ | H | 0 | — | — | 6.6 | 25.0 | 69.4 | — | 5.76 | (4.24–7.82) |
| VAL 47-078 | N | 1 | 2-(CH=CH) | H | H | 0 | — | — | 11.2 | 41.3 | 78.6 | — | 3.85 | (2.70–5.50) |
| VAL 47-055 | N | 2 | 2-(CH=CH) | H | H | 0 | — | 5.6 | 47.5 | 85.9 | — | — | 1.54 | (1.11–2.14) |
| VAL 47-017 | N | 2 | 3-(CH=CH) | H | H | 0 | — | 45.7 | 71.6 | 93.9 | 100 | — | 0.36 | (0.19–0.71) |
| VAL 47-042 | N | 2 | 4-(CH=CH) | H | H | 0 | — | 3.9 | 41.7 | 77.8 | — | — | 1.28 | (0.95–1.75) |
| VAL 47-022 | N | 1 | 3-(CH=CH) | H | H | 4 | — | 3.9 | 43.4 | 97.1 | — | — | 1.01 | (0.85–1.20) |
| VAL 47-067 | N | 2 | 4-(CH=CH) | H | H | 4 | 1.1 | 53.6 | 81.8 | — | — | — | 0.35 | (0.25–0.49) | n.d. not determinable
N.B. unless otherwise specified, the double bond in X is in trans configuration

TABLE 2

ANTIALLERGIC ACTIVITY IN THE RAT
PCA Test
Oral administration
5 minutes before challenge with antigen

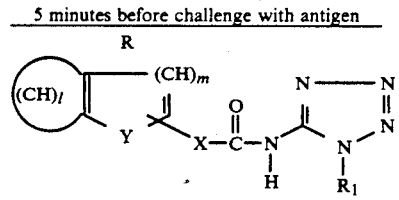

| | | | | | | | mg/kg/iv | | | | | | |
|---|---|---|---|---|---|---|---|---|---|---|---|---|---|
| | | | | | | 0.3 | 1 | 3 | 10 | 30 | $ED_{50}$ | (conf. lim) |
| COMPOUND | Y | m | X | R | $R_1$ | l | | inhibition (%) | | | | (mg/kg/iv) | P = 0.05 |
| TRANILAST | ... | ... | ... | ... | ... | ... | administered 15 minutes before challenge with antigen | | | | | 115.1 | (43.0–307.6) |
| TA 57-07 | ... | ... | ... | ... | ... | ... | 12.7 | 57.7 | 82.5 | — | — | 0.93 | (0.61–1.42) |
| VAL 47-024 | S | 1 | 2-(CH=CH) | H | H | 0 | — | — | 30.2 | 53.8 | 53.3 | n.d. | |
| VAL 47-005 | S | 1 | 2-(CH=CH) | 5-$CH_3$ | H | 0 | — | — | 9.6 | 43.8 | 75.3 | 12.36 | (8.36–18.30) |
| VAL 47-005Na | S | 1 | 2-(CH=CH) | 5-$CH_3$ | Na | 0 | — | — | 26.7 | 54.7 | 65.8 | 10.19 | (4.37–23.75) |
| VAL 47-005cis | S | 1 | 2-(CH=CH) | 5-$CH_3$ | H | 0 | 23.6 | 51.1 | 94.5 | — | — | 0.78 | (0.56–1.12) |
| VAL 47-008 | S | 1 | 2-(CH=CH) | 5-Br | H | 0 | — | — | 32.5 | 26.9 | 43.7 | n.d. | |

TABLE 2-continued

ANTIALLERGIC ACTIVITY IN THE RAT
PCA Test
Oral administration
5 minutes before challenge with antigen

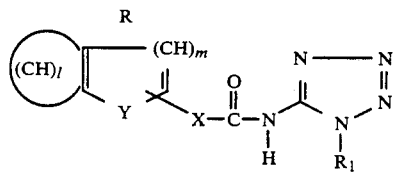

| COMPOUND | Y | m | X | R | $R_1$ | l | 0.3 | 1 | 3 | 10 | 30 | $ED_{50}$ (mg/kg/iv) | (conf. lim) P = 0.05 |
|---|---|---|---|---|---|---|---|---|---|---|---|---|---|
| | | | | | | | | | inhibition (%) | | | | |
| VAL 47-034 | S | 1 | 3-(CH=CH) | H | H | 0 | — | — | 0 | 0 | 53.4 | n.d. | |
| VAL 47-010 | O | 1 | 2-(CH=CH) | H | H | 0 | — | — | 9.6 | 35.9 | 80.9 | 12.37 | (9.06–16.90) |
| VAL 47-073 | O | 1 | 2-(CH=CH) | 5-$CH_3$ | H | 0 | 22.0 | 44.0 | 87.5 | 89.3 | — | 0.92 | (0.69–1.22) |
| VAL 47-073cis | O | 1 | 2-(CH=CH) | 5-$CH_3$ | H | 0 | 25.1 | 42.6 | 67.2 | — | — | 1.26 | (0.75–2.11) |
| VAL 47-078 | N | 1 | 2-(CH=CH) | H | H | 0 | — | — | 7.4 | 35.8 | 38.3 | n.d. | |
| VAL 47-055 | N | 2 | 2-(CH=CH) | H | H | 0 | — | 22.5 | 28.3 | 52.9 | 81.0 | 7.94 | (4.29–14.69) |
| VAL 47-017 | N | 2 | 3-(CH=CH) | H | H | 0 | — | — | 21.7 | 22.8 | 48.3 | n.d. | |
| VAL 47-042 | N | 2 | 4-(CH=CH) | H | H | 0 | — | — | 0 | 5.3 | 21.4 | n.d. | |
| VAL 47-022 | N | 1 | 3-(CH=CH) | H | H | 4 | — | — | 17.8 | 46.6 | 40.8 | n.d. | |
| VAL 47-067 | N | 2 | 4-(CH=CH) | H | H | 4 | — | — | 8.3 | 0 | 16.7 | n.d. | | n.d. not determinable
N.B. unless otherwise specified, the double bond in X is in trans configuration

TABLE 3

ANTIALLERGIC ACTIVITY IN THE RAT
PCA Test
Time response curve
after oral administration

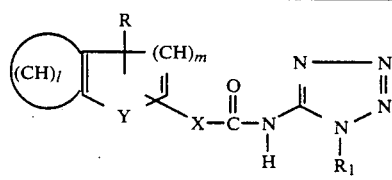

| COMPOUND | Y | m | X | R | $R_1$ | l | ADMINISTERED DOSE (mg/kg/os) | 5 | 15 | 30 | 60 | 120 |
|---|---|---|---|---|---|---|---|---|---|---|---|---|
| | | | | | | | | | | (inhibition %) | | |
| TRANILAST | ... | ... | ... | ... | ... | ... | 100 | 17.9 | 37.4 | 20.5 | 20.5 | 13.7 |
| TA 57-07 | ... | ... | ... | ... | ... | ... | 1 | 86.8 | 43.7 | 37.6 | 17.3 | 4.1 |
| VAL 47-024 | S | 1 | 2-(CH=CH) | H | H | 0 | 30 | 43.5 | 52.7 | 46.7 | 30.4 | 10.9 |
| VAL 47-005 | S | 1 | 2-(CH=CH) | 5-$CH_3$ | H | 0 | 30 | 75.5 | 61.4 | 37.5 | 0 | 11.4 |
| VAL 47-005cis | S | 1 | 2-(CH=CH) | 5-$CH_3$ | H | 0 | 1 | 52.4 | 27.5 | 20.6 | 19.6 | 2.10 |
| VAL 47-008 | S | 1 | 2-(CH=CH) | 5-Br | H | 0 | 30 | 37.7 | 16.0 | 10.9 | 3.4 | 2.3 |
| VAL 47-034 | S | 1 | 3-(CH=CH) | H | H | 0 | 30 | 64.5 | 36.0 | 41.9 | 6.9 | 0 |
| VAL 47-010 | O | 1 | 2-(CH=CH) | H | H | 0 | 30 | 51.4 | 44.8 | 21.9 | 6.6 | 18.6 |
| VAL 47-073 | O | 1 | 2-(CH=CH) | 5-$CH_3$ | H | 0 | 1 | 52.6 | 7.8 | 19.8 | 0 | 0 |
| VAL 47-073cis | O | 1 | 2-(CH=CH) | 5-$CH_3$ | H | 0 | 3 | 50.8 | 66.4 | 17.3 | 5.8 | 0 |
| VAL 47-078 | N | 1 | 2-(CH=CH) | H | H | 0 | 30 | 31.4 | 29.3 | 9.0 | 4.3 | 0.5 |
| VAL 47-055 | N | 2 | 2-(CH=CH) | H | H | 0 | 10 | 45.6 | 0.5 | 0 | 4.7 | 0 |
| VAL 47-017 | N | 2 | 3-(CH=CH) | H | H | 0 | 30 | 45 | 7.3 | 1 | 0 | 0 |
| VAL 47-042 | N | 2 | 4-(CH=CH) | H | H | 0 | 30 | 6.3 | 0 | 0.5 | 0 | 0 |
| VAL 47-022 | N | 1 | 3-(CH=CH) | H | H | 4 | 30 | 62.2 | 52.7 | 33.3 | 19.4 | 8.9 |
| VAL 47-067 | N | 2 | 4-(CH=CH) | H | H | 4 | 30 | 50.5 | 29.3 | 13.3 | 0 | 0 |

N.B. unless otherwise specified, the double bond in X is in trans configuration

TABLE 4

ACUTE TOXICITY IN THE MOUSE
Oral administration

| COMPOUND | Y | m | X | R | R₁ | l | ADMINISTERED DOSE (mg/kg/os) | No. TREATED | No. DEAD | % |
|---|---|---|---|---|---|---|---|---|---|---|
| TRANILAST | ... | ... | ... | ... | ... | ... | 1000 | 8 | 7 | 87.5 |
| TA 57-07 | ... | ... | ... | ... | ... | ... | 1000 | 8 | 4 | 50 |
| VAL 47-024 | S | 1 | 2-(CH=CH) | H | H | 0 | 1000 | 8 | 0 | 0 |
| VAL 47-005 | S | 1 | 2-(CH=CH) | 5-CH₃ | H | 0 | 1000 | 8 | 0 | 0 |
| VAL 47-005Na | S | 1 | 2-(CH=CH) | 5-CH₃ | Na | 0 | 1000 | 8 | 0 | 0 |
| VAL 47-005cis | S | 1 | 2-(CH=CH) | 5-CH₃ | H | 0 | 1000 | 8 | 0 | 0 |
| VAL 47-008 | S | 1 | 2-(CH=CH) | 5-Br | H | 0 | 1000 | 8 | 0 | 0 |
| VAL 47-034 | S | 1 | 3-(CH=CH) | H | H | 0 | 1000 | 8 | 2 | 25 |
| VAL 47-010 | O | 1 | 2-(CH=CH) | H | H | 0 | 1000 | 8 | 2 | 25 |
| VAL 47-073 | O | 1 | 2-(CH=CH) | 5-CH₃ | H | 0 | 1000 | 8 | 0 | 0 |
| VAL 47-073cis | O | 1 | 2-(CH=CH) | 5-CH₃ | H | 0 | 1000 | 8 | 1 | 12.5 |
| VAL 47-078 | N | 1 | 2-(CH=CH) | H | H | 0 | 1000 | 8 | 0 | 0 |
| VAL 47-055 | N | 2 | 2-(CH=CH) | H | H | 0 | 1000 | 8 | 0 | 0 |
| VAL 47-017 | N | 2 | 3-(CH=CH) | H | H | 0 | 1000 | 8 | 0 | 0 |
| VAL 47-042 | N | 2 | 4-(CH=CH) | H | H | 0 | 1000 | 8 | 0 | 0 |
| VAL 47-022 | N | 1 | 3-(CH=CH) | H | H | 4 | 1000 | 8 | 0 | 0 |
| VAL 47-067 | N | 2 | 4-(CH=CH) | H | H | 4 | 1000 | 8 | 1 | 12.5 |

N.B. unless otherwise specified, the double bond in X is in trans configuration

What is claimed is:

1. Tetrazole amide derivatives of the formula (I):

in which
Y=NH, O or S when m=1;
Y=N when m=2;
m=1 or 2;
l=0 or 4;
R=H, C₁₋₄ alkyl, Cl, Br, CF₃, CH₂OCOCH₃, or OCH₂-Ph;
R₁=H, alkaline metal or alkaline earth metal;
the double bond of the alkenyl chain being of trans or cis configuration and the possible benzene ring being unsubstituted.

2. A derivative as claimed in claim 1, consisting of N-1H-tetrazol-5-yl-[3-[5-methyl-(2-thienyl)]]-acrylamide trans isomer.

3. A derivative as claimed in claim 1, consisting of N-1H-tetrazol-5-yl-[3-[5-methyl-(2-thienyl)]]-acrylamide trans isomer sodium salt.

4. A derivative as claimed in claim 1, consisting of N-1H-tetrazol-5-yl-[3-(2-thienyl)]-acrylamide trans isomer.

5. A derivative as claimed in claim 1, consisting of N-1H-tetrazol-5-yl-[5-bromo-(2-thienyl)]-acrylamide trans isomer.

6. A derivative as claimed in claim 1, consisting of N-1H-tetrazol-5-yl-[3-(3-thienyl)]-acrylamide trans isomer.

7. A derivative as claimed in claim 1, consisting of N-1H-tetrazol-5-yl-[3-[5-ethyl-(3-thienyl)]]-acrylamide trans isomer.

8. A derivative as claimed in claim 1, consisting of N-1H-tetrazol-5-yl-[3-(2-pyrrole)]-acrylamide trans isomer.

9. A derivative as claimed in claim 1, consisting of N-1H-tetrazol-5-yl-[3-(2-pyridyl)]-acrylamide trans isomer.

10. A derivative as claimed in claim 1, consisting of N-1H-tetrazol-5-yl-[3-[6-chloro-(2-pyridyl)]]-acrylamide trans isomer.

11. A derivative as claimed in claim 1, consisting of N-1H-tetrazol-5-yl-[3-(3-pyridyl)]-acrylamide trans isomer.

12. A derivative as claimed in claim 1, consisting of N-1H-tetrazol-5-yl-[3-(4-pyridyl)]-acrylamide trans isomer.

13. A derivative as claimed in claim 1, consisting of N-1H-tetrazol-5-yl-[3-(2-furyl)]-acrylamide trans isomer.

14. A derivative as claimed in claim 1, consisting of N-1H-tetrazol-5-yl-[3-[5-methyl-(2-furyl)]]-acrylamide trans isomer.

15. A derivative as claimed in claim 1, consisting of N-1H-tetrazol-5-yl-[3-(3-indolyl)]-acrylamide trans isomer.

16. A derivative as claimed in claim 1, consisting of N-1H-tetrazol-5-yl-[3-(2-quinolyl)]-acrylamide trans isomer.

17. A derivative as claimed in claim 1, consisting of N-1H-tetrazol-5-yl-[3-(4-quinolyl)]-acrylamide trans isomer.

18. A derivative as claimed in claim 1, consisting of N-1H-tetrazol-5-yl-[3-[5-methyl-(2-thienyl)]]-acrylamide cis isomer.

19. A derivative as claimed in claim 1, consisting of N-1H-tetrazol-5-yl-[3-[5-methyl-(2-furyl)]]-acrylamide cis isomer.

20. Pharmaceutical compositions comprising one or more tetrazole amide derivatives of formula (I) according to claim 1 as active substances in association with diluent and exoipient substances normally used in pharmaceutics.

21. A method of anti-allergic treatment which comprises administering an anti-allergical effective amount of a tetrazole amide derivative of formula I according to claim 1.

* * * * *